(12) United States Patent
Neumann

(10) Patent No.: US 11,728,017 B2
(45) Date of Patent: Aug. 15, 2023

(54) METHODS AND SYSTEMS FOR PHYSIOLOGICALLY INFORMED THERAPEUTIC PROVISIONS

(71) Applicant: KPN Innovations, LLC, Lakewood, CO (US)

(72) Inventor: Kenneth Neumann, Lakewood, CO (US)

(73) Assignee: KPN INNOVATIONS, LLC., Lakewood, CO (US)

( * ) Notice: Subject to any disclaimer, the term of this patent is extended or adjusted under 35 U.S.C. 154(b) by 796 days.

(21) Appl. No.: 16/778,994

(22) Filed: Jan. 31, 2020

(65) Prior Publication Data
US 2021/0241872 A1    Aug. 5, 2021

(51) Int. Cl.
| | |
|---|---|
| *G16H 20/00* | (2018.01) |
| *G16H 10/60* | (2018.01) |
| *G16H 50/20* | (2018.01) |
| *G16H 70/20* | (2018.01) |
| *G16H 40/67* | (2018.01) |
| *G06N 20/00* | (2019.01) |
| *G16H 70/60* | (2018.01) |

(52) U.S. Cl.
CPC ............ *G16H 20/00* (2018.01); *G06N 20/00* (2019.01); *G16H 10/60* (2018.01); *G16H 40/67* (2018.01); *G16H 50/20* (2018.01); *G16H 70/20* (2018.01); *G16H 70/60* (2018.01)

(58) Field of Classification Search
CPC ........ G16H 20/00; G16H 50/20; G16H 10/60; G16H 70/20
See application file for complete search history.

(56) References Cited

U.S. PATENT DOCUMENTS

| | | | |
|---|---|---|---|
| 11,484,273 B2 * | 11/2022 | Kochura | A61B 5/7275 |
| 2014/0058755 A1 | 2/2014 | Macoviak et al. | |

(Continued)

OTHER PUBLICATIONS

Jo Best, AI, MD: Five unexpected ways that artificial intelligence will make your healthcare better, Website, Oct. 23, 2019 https://www.zdnet.com/article/ai-md-five-unexpected-ways-that-artificial-intelligence-will-make-your-healthcare-better/.

*Primary Examiner* — Evangeline Barr
(74) *Attorney, Agent, or Firm* — Caldwell Intellectual Property Law

(57) ABSTRACT

A system for physiologically informed therapeutic provisions includes a computing device configured to receive, from a remote device operated by a user, a conditional datum wherein the conditional datum contains a description of a current bodily complaint. The computing device is further configured to identify a plurality of antidotal therapeutic provisions, using a therapeutic clustering model wherein the therapeutic clustering model utilizes a conditional datum as an input and outputs antidotal therapeutic provisions. The computing device is further configured to locate a user biological extraction wherein the user biological extraction contains at least an element of user physiological data. The computing device is further configured to generate a compatibility model, wherein the compatibility model utilizes the antidotal therapeutic provisions and the user biological extraction as an input and outputs compatible antidotal therapeutic provisions.

18 Claims, 6 Drawing Sheets

(56) References Cited

U.S. PATENT DOCUMENTS

| | | |
|---|---|---|
| 2014/0278546 A1* | 9/2014 | Op Den Buijs ....... G16H 10/60 705/3 |
| 2014/0279746 A1* | 9/2014 | De Bruin ............... G16H 10/60 706/46 |
| 2016/0314432 A1 | 10/2016 | Bhatti |
| 2018/0137462 A1 | 5/2018 | Zohar et al. |
| 2019/0172012 A1 | 6/2019 | Roy |
| 2019/0206540 A1 | 7/2019 | Agassi et al. |
| 2019/0244164 A1 | 8/2019 | Emert |
| 2019/0304000 A1* | 10/2019 | Simpson .......... G01N 33/48792 |
| 2019/0355450 A1 | 11/2019 | Altstadter et al. |
| 2019/0392924 A1* | 12/2019 | Bettencourt-Silva ........................ G16H 50/70 |

* cited by examiner

METHODS AND SYSTEMS FOR PHYSIOLOGICALLY INFORMED THERAPEUTIC PROVISIONS

FIELD OF THE INVENTION

The present invention generally relates to the field of artificial intelligence. In particular, the present invention is directed to methods and systems for physiologically informed therapeutic provisions.

BACKGROUND

Accurate selection and utilizing of a therapeutic provision can be challenging. Often an incorrect therapeutic provision may be administered that is temporary and only remedies a problem for a short duration. In addition, there may be other available therapeutic provisions that may be better tolerated and provide superior results. Currently, there remains to be seen a way to inform a user that a therapeutic provision is suitable based on a user's own unique physiological information and for an intended medical purpose.

SUMMARY OF THE DISCLOSURE

A system for physiologically informed therapeutic provisions, the system comprising a computing device the computing device designed and configured to receive, from a remote device operated by a user, a conditional datum, wherein the conditional datum contains a description of a current bodily complaint. The computing device is further configured to identify a plurality of antidotal therapeutic provisions, using a therapeutic clustering model, wherein the therapeutic clustering model utilizes a conditional datum as an input and outputs antidotal therapeutic provisions. The computing device is further configured to locate a user biological extraction, wherein the user biological extraction contains at least an element of user physiological data. The computing device is further configured to generate a compatibility model, wherein the compatibility model utilizes the antidotal therapeutic provisions and the user biological extraction as an input and outputs compatible antidotal therapeutic provisions.

A method of physiologically informed therapeutic provisions, the method comprising receiving, by a computing device, from a remote device operated by a user, a conditional datum, wherein the conditional datum contains a description of a current bodily complaint. The method further comprises identifying by the computing device, a plurality of antidotal therapeutic provisions, using a therapeutic clustering model, wherein the therapeutic clustering model utilizes a conditional datum as an input and outputs antidotal therapeutic provisions. The method further comprises locating by the computing device, a user biological extraction, wherein the user biological extraction contains at least an element of user physiological data. The method further comprises generating by the computing device, a compatibility model wherein the compatibility model utilizes the antidotal therapeutic provisions and the user biological extraction as an input and outputs compatible antidotal therapeutic provisions.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for physiologically informed therapeutic provisions. In an embodiment, a computing device receives a conditional datum containing a description of a current bodily complaint. For instance and without limitation, a conditional datum may indicate that a user has previously been diagnosed with osteoarthritis. In yet another non-limiting example, a conditional datum may indicate that a user has a laceration on the user's left upper thigh. A computing device uses a therapeutic clustering model to identify a plurality of antidotal therapeutic provisions. For example, a computing device may use a therapeutic clustering model to identify for a conditional datum such as Type 1 Diabetes Mellitus a plurality of antidotal therapeutic provisions including an insulin pump, insulin pen, insulin syringe, infusion pump, and a glucose meter. Computing device locates a user biological extraction stored within a database that contains at least an element of user physiological data. Computing device generates a compatibility model using a first machine-learning algorithm. Compatibility model utilizes output antidotal therapeutic provisions and a user biological extraction as an input and outputs compatible antidotal therapeutic provisions.

Figure 1:
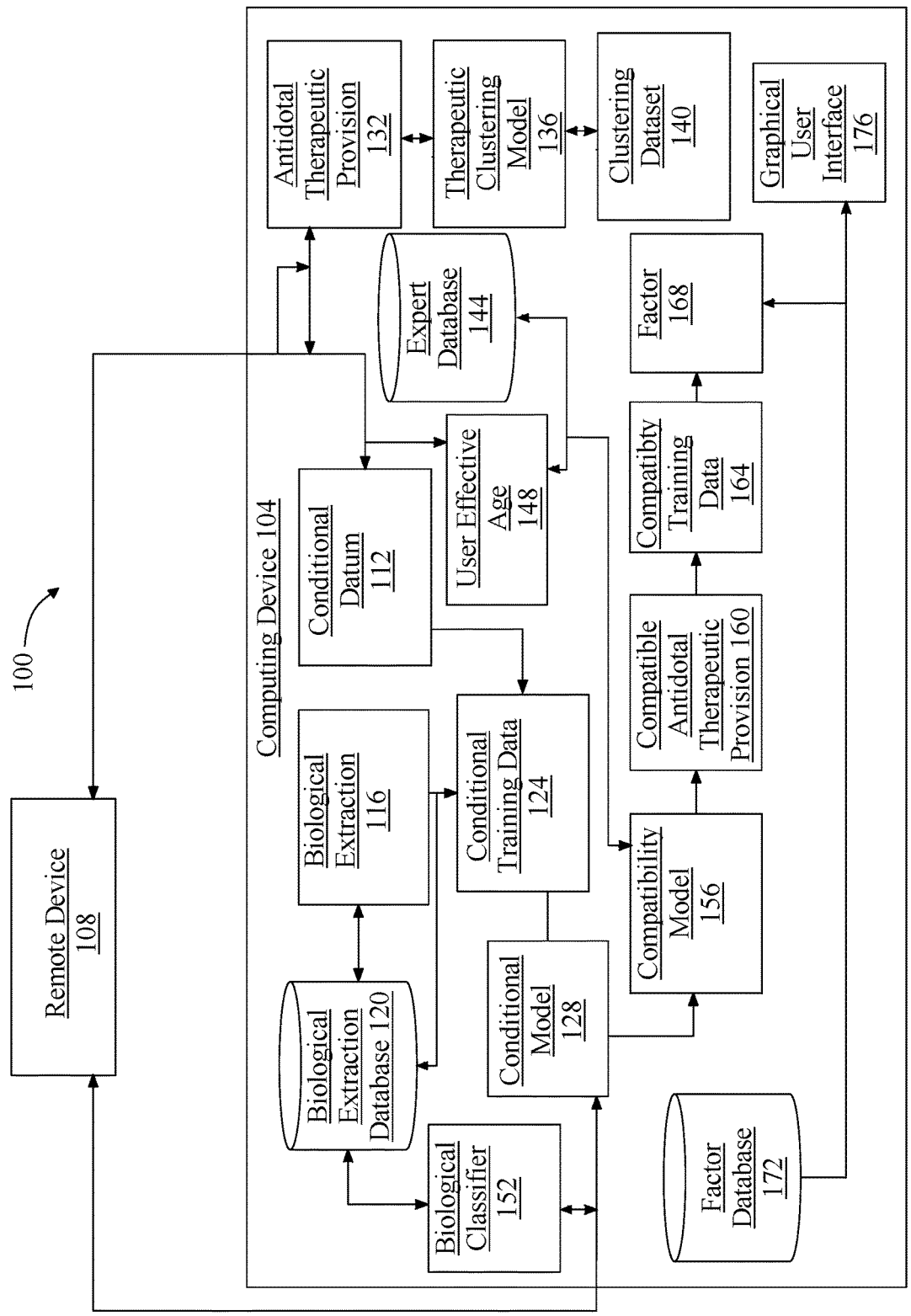
FIG. 1 is a block diagram illustrating an exemplary embodiment of a system for physiologically informed therapeutic provisions.

Referring now to FIG. 1, an exemplary embodiment of a system 100 for physiologically informed therapeutic provisions is illustrated. System 100 includes a computing device 104. Computing device 104 may include any computing device 104 as described in this disclosure, including without limitation a microcontroller, microprocessor, digital signal processor (DSP) and/or system on a chip (SoC) as described in this disclosure. Computing device 104 may include, be included in, and/or communicate with a mobile device such as a mobile telephone or smartphone. Computing device 104 may include a single computing device 104 operating independently or may include two or more computing device 104 operating in concert, in parallel, sequentially or the like;

two or more computing devices 104 may be included together in a single computing device 104 or in two or more computing devices 104. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices 104, and any combinations thereof. A network may employ a wired and/or a wireless mode of communication. In general, any network topology may be used. Information (e.g., data, software etc.) may be communicated to and/or from a computer and/or a computing device 104. Computing device 104 may include but is not limited to, for example, a computing device 104 or a cluster of computing devices 104 in a first location and a second computing device 104 or cluster of computing devices 104 in a second location. Computing device 104 may include one or more computing devices 104 dedicated to data storage, security, distribution of traffic for load balancing, and the like. Computing device 104 may distribute one or more computing tasks as described below across a plurality of computing devices 104 of computing device 104, which may operate in parallel, in series, redundantly, or in any other manner used for distribution of tasks or memory between computing devices 104. Computing device 104 may be implemented using a "shared nothing" architecture in which data is cached at the worker; in an embodiment, this may enable scalability of system 100 and/or computing device 104.

Still referring to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, computing device 104 is configured to receive from a remote device 108 operated by a user, a conditional datum. Remote device 108 may include without limitation, a display in communication with computing device 104, where a display may include any display as described herein. Remote device 108 may include an additional computing device, such as a mobile device, laptop, desktop, computer and the like. Remote device 108 may be operated by a user, where a user may include any human being. Computing device 104 may receive a transmission from a remote device 108 utilizing any network methodology as described herein. A "conditional datum," as used in this disclosure, is any data describing a current bodily complaint. A currently bodily complaint may include a bodily disorder, disease, malady, ailment, symptom, medical diagnosis, physical or mental feature regarded as indicating a condition of disease, evidence of disease or a physical disturbance, and the like. A conditional datum 112 may describe a current medical diagnosis of Type 2 Diabetes Mellitus. A conditional datum 112 may describe a previous diagnosis of total paralysis. A conditional datum 112 may describe a series of symptoms that include loud snoring, daytime sleepiness and fatigue, unrefreshed sleep, insomnia, and morning headaches. A conditional datum 112 may describe a flare up of recurrent symptoms associated with a previously diagnosed medical condition such as rheumatoid arthritis. A conditional datum 112 may describe an acute disease such as a short-lived disease such as the common cold. A conditional datum 112 may describe a chronic disease that may last a long time and may go into remission and periodically relapse such as gout or ulcerative colitis. A conditional datum 112 may describe a progressive disease that may worsen until death such as pancreatic cancer, Alzheimer's disease, muscular dystrophy, and/or multiple sclerosis. A conditional datum 112 may describe a refractory disease that may resist treatment such as hormone-refractory prostate cancer. A conditional datum 112 may describe a subclinical disease such as a silent disease or asymptomatic disease that occurs when disease happens before symptoms are first noted such as hypertension, hyperlipidemia, and/or coronary artery disease. A conditional datum 112 may describe a localized disease that may only affect one part of the body such as athlete's foot or an eye infection. A conditional datum 112 may describe a disseminated disease that may have spread to other parts of the body such as metastatic cancer. A conditional datum 112 may describe a systemic disease that affects the entire body such as influenza, diabetes, and/or obesity.

With continued reference to FIG. 1, computing device 104 is configured to receive from a remote device 108 operated by an informed advisor, a conditional datum 112. A "informed advisor," as used in this disclosure, is any medical professional who provides medical treatment to a user. An informed advisor may include a medical doctor, nurse, physician assistant, nurse practitioner, pharmacist, chiropractor, yoga instructor, life coach, nutritionist, dietician, therapist, administrative staff, physical therapists, occupational therapists, speech therapists, alternative medicine practitioners, foot care practitioners, public health practitioners and the like. An informed advisor may provide medical treatment when the informed advisor is involved in any aspect of the user's medical care. For instance and without limitation, an informed advisor such as a pharmacist may provide medical treatment when the pharmacist dispenses a prescription medication to the user. In yet another non-limiting example, an informed advisor such as a yoga instructor may provide medical treatment when the yoga instructor teaches the user a yoga class. Computing device 104 may receive a conditional datum 112 from a remote device 108 operated by an informed advisor that contains a current bodily diagnosis. A "current bodily diagnosis," as used in this disclosure, is data that describes a disease and/or condition that a user is afflicted with. A current bodily diagnosis is generated by one or more informed advisors. A current bodily diagnosis may be based on one or more user reported symptoms. A current bodily diagnosis may be based on one or more laboratory reports and/or test results. A current bodily diagnosis may be based on one or more medical imaging studies. A current bodily diagnosis may be based on a tissue examination including any macroscopic, microscopic, and/or molecular examination of tissues including biopsies. A current bodily diagnosis may be based on diagnostic criteria that may include any medical standards published by international committees that may offer criteria that may be used to determine a diagnosis based on any combination of signs, symptoms, and test results that an informed advisor uses to determine a correct diagnosis. A current bodily diagnosis may be based on a prenatal diagnosis for work done before birth. A current bodily diagnosis may be based on a diagnosis of exclusion, where a medical condition cannot be established with complete confidence from a history, examination or testing and diagnosis is therefore created by an elimination of all other reasonable possibilities. A current bodily diagnosis may be based on a dual diagnosis of two related but separate medical conditions or co-morbidities such as a mental disorder and a substance abuse addiction.

With continued reference to FIG. 1, computing device 104 is configured to generate a conditional datum 112 using one or more machine-learning processes and/or algorithms. Computing device 104 is configured to retrieve a biological extraction 116. A "biological extraction," as used in this disclosure, contains at least an element of user physiological data. As used in this disclosure, "physiological data" is any data indicative of a person's physiological state; physiological state may be evaluated with regard to one or more measures of health of a person's body, one or more systems within a person's body such as a circulatory system, a digestive system, a nervous system, or the like, one or more organs within a person's body, and/or any other subdivision of a person's body useful for diagnostic or prognostic purposes. For instance, and without limitation, a particular set of biomarkers, test results, and/or biochemical information may be recognized in a given medical field as useful for identifying various disease conditions or prognoses within a relevant field. As a non-limiting example, and without limitation, physiological data describing red blood cells, such as red blood cell count, hemoglobin levels, hematocrit, mean corpuscular volume, mean corpuscular hemoglobin, and/or mean corpuscular hemoglobin concentration may be recognized as useful for identifying various conditions such as dehydration, high testosterone, nutrient deficiencies, kidney dysfunction, chronic inflammation, anemia, and/or blood loss.

With continued reference to FIG. 1, physiological state data may include, without limitation, hematological data, such as red blood cell count, which may include a total number of red blood cells in a person's blood and/or in a blood sample, hemoglobin levels, hematocrit representing a percentage of blood in a person and/or sample that is composed of red blood cells, mean corpuscular volume, which may be an estimate of the average red blood cell size, mean corpuscular hemoglobin, which may measure average weight of hemoglobin per red blood cell, mean corpuscular hemoglobin concentration, which may measure an average concentration of hemoglobin in red blood cells, platelet count, mean platelet volume which may measure the average size of platelets, red blood cell distribution width, which measures variation in red blood cell size, absolute neutrophils, which measures the number of neutrophil white blood cells, absolute quantities of lymphocytes such as B-cells, T-cells, Natural Killer Cells, and the like, absolute numbers of monocytes including macrophage precursors, absolute numbers of eosinophils, and/or absolute counts of basophils. Physiological state data may include, without limitation, immune function data such as Interleukine-6 (IL-6), TNF-alpha, systemic inflammatory cytokines, and the like.

Continuing to refer to FIG. 1, physiological state data may include, without limitation, data describing blood-born lipids, including total cholesterol levels, high-density lipoprotein (HDL) cholesterol levels, low-density lipoprotein (LDL) cholesterol levels, very low-density lipoprotein (VLDL) cholesterol levels, levels of triglycerides, and/or any other quantity of any blood-born lipid or lipid-containing substance. Physiological state data may include measures of glucose metabolism such as fasting glucose levels and/or hemoglobin A1-C(HbA1c) levels. Physiological state data may include, without limitation, one or more measures associated with endocrine function, such as without limitation, quantities of dehydroepiandrosterone (DHEAS), DHEA-Sulfate, quantities of cortisol, ratio of DHEAS to cortisol, quantities of testosterone quantities of estrogen, quantities of growth hormone (GH), insulin-like growth factor 1 (IGF-1), quantities of adipokines such as adiponectin, leptin, and/or ghrelin, quantities of somatostatin, progesterone, or the like. Physiological state data may include measures of estimated glomerular filtration rate (eGFR). Physiological state data may include quantities of C-reactive protein, estradiol, ferritin, folate, homocysteine, prostate-specific Ag, thyroid-stimulating hormone, vitamin D, 25 hydroxy, blood urea nitrogen, creatinine, sodium, potassium, chloride, carbon dioxide, uric acid, albumin, globulin, calcium, phosphorus, alkaline phosphatase, alanine amino transferase, aspartate amino transferase, lactate dehydrogenase (LDH), bilirubin, gamma-glutamyl transferase (GGT), iron, and/or total iron binding capacity (TIBC), or the like. Physiological state data may include antinuclear antibody levels. Physiological state data may include aluminum levels. Physiological state data may include arsenic levels. Physiological state data may include levels of fibrinogen, plasma cystatin C, and/or brain natriuretic peptide.

Continuing to refer to FIG. 1, physiological state data may include measures of lung function such as forced expiratory volume, one second (FEV-1) which measures how much air can be exhaled in one second following a deep inhalation, forced vital capacity (FVC), which measures the volume of air that may be contained in the lungs. Physiological state data may include a measurement blood pressure, including without limitation systolic and diastolic blood pressure. Physiological state data may include a measure of waist circumference. Physiological state data may include body mass index (BMI). Physiological state data may include one or more measures of bone mass and/or density such as dual-energy x-ray absorptiometry. Physiological state data may include one or more measures of muscle mass. Physiological state data may include one or more measures of physical capability such as without limitation measures of grip strength, evaluations of standing balance, evaluations of gait speed, pegboard tests, timed up and go tests, and/or chair rising tests.

Still viewing FIG. 1, physiological state data may include one or more measures of cognitive function, including without limitation Rey auditory verbal learning test results, California verbal learning test results, NIH toolbox picture sequence memory test, Digital symbol coding evaluations, and/or Verbal fluency evaluations. Physiological state data may include one or more evaluations of sensory ability, including measures of audition, vision, olfaction, gustation, vestibular function and pain.

Continuing to refer to FIG. 1, physiological state data may include psychological data. Psychological data may include any data generated using psychological, neuro-psychological, and/or cognitive evaluations, as well as diagnostic screening tests, personality tests, personal compatibility tests, or the like; such data may include, without limitation, numerical score data entered by an evaluating professional and/or by a subject performing a self-test such as a computerized questionnaire. Psychological data may include textual, video, or image data describing testing, analysis, and/or conclusions entered by a medical professional such as without limitation a psychologist, psychiatrist, psychotherapist, social worker, a medical doctor, or the like. Psychological data may include data gathered from user interactions with persons, documents, and/or computing devices; for instance, user patterns of purchases, including electronic purchases, communication such as via chat-rooms or the like, any textual, image, video, and/or data produced by the subject, any textual image, video and/or other data depicting and/or describing the subject, or the like. Any psychological data and/or data used to generate psychological data may be analyzed using machine-learning and/or language processing module 136 as described in this disclosure.

Still referring to FIG. 1, physiological state data may include genomic data, including deoxyribonucleic acid (DNA) samples and/or sequences, such as without limitation DNA sequences contained in one or more chromosomes in human cells. Genomic data may include, without limitation, ribonucleic acid (RNA) samples and/or sequences, such as samples and/or sequences of messenger RNA (mRNA) or the like taken from human cells. Genetic data may include telomere lengths. Genomic data may include epigenetic data including data describing one or more states of methylation of genetic material. Physiological state data may include proteomic data, which as used herein is data describing all proteins produced and/or modified by an organism, colony of organisms, or system of organisms, and/or a subset thereof. Physiological state data may include data concerning a microbiome of a person, which as used herein includes any data describing any microorganism and/or combination of microorganisms living on or within a person, including without limitation biomarkers, genomic data, proteomic data, and/or any other metabolic or biochemical data useful for analysis of the effect of such microorganisms on other physiological state data of a person, as described in further detail below.

With continuing reference to FIG. 1, physiological state data may include one or more user-entered descriptions of a person's physiological state. One or more user-entered descriptions may include, without limitation, user descriptions of symptoms, which may include without limitation current or past physical, psychological, perceptual, and/or neurological symptoms, user descriptions of current or past physical, emotional, and/or psychological problems and/or concerns, user descriptions of past or current treatments, including therapies, nutritional regimens, exercise regimens, pharmaceuticals or the like, or any other user-entered data that a user may provide to a medical professional when seeking treatment and/or evaluation, and/or in response to medical intake papers, questionnaires, questions from medical professionals, or the like. Physiological state data may include any physiological state data, as described above, describing any multicellular organism living in or on a person including any parasitic and/or symbiotic organisms living in or on the persons; non-limiting examples may include mites, nematodes, flatworms, or the like. Examples of physiological state data described in this disclosure are presented for illustrative purposes only and are not meant to be exhaustive.

With continued reference to FIG. 1, physiological data may include, without limitation any result of any medical test, physiological assessment, cognitive assessment, psychological assessment, or the like. System 100 may receive at least a physiological data from one or more other devices after performance; system 100 may alternatively or additionally perform one or more assessments and/or tests to obtain at least a physiological data, and/or one or more portions thereof, on system 100. For instance, at least physiological data may include or more entries by a user in a form or similar graphical user interface 176 object; one or more entries may include, without limitation, user responses to questions on a psychological, behavioral, personality, or cognitive test. For instance, at least a server 104 may present to user a set of assessment questions designed or intended to evaluate a current state of mind of the user, a current psychological state of the user, a personality trait of the user, or the like; at least a server 104 may provide user-entered responses to such questions directly as at least a physiological data and/or may perform one or more calculations or other algorithms to derive a score or other result of an assessment as specified by one or more testing protocols, such as automated calculation of a Stanford-Binet and/or Wechsler scale for IQ testing, a personality test scoring such as a Myers-Briggs test protocol, or other assessments that may occur to persons skilled in the art upon reviewing the entirety of this disclosure.

With continued reference to FIG. 1, assessment and/or self-assessment data, and/or automated or other assessment results, obtained from a third-party device; third-party device may include, without limitation, a server or other device (not shown) that performs automated cognitive, psychological, behavioral, personality, or other assessments. Third-party device may include a device operated by an informed advisor. An informed advisor may include any medical professional who may assist and/or participate in the medical treatment of a user. An informed advisor may include a medical doctor, nurse, physician assistant, pharmacist, yoga instructor, nutritionist, spiritual healer, meditation teacher, fitness coach, health coach, life coach, and the like.

With continued reference to FIG. 1, physiological data may include data describing one or more test results, including results of mobility tests, stress tests, dexterity tests, endocrinal tests, genetic tests, and/or electromyographic tests, biopsies, radiological tests, genetic tests, and/or sensory tests. Persons skilled in the art, upon reviewing the entirety of this disclosure, will be aware of various additional examples of at least a physiological sample consistent with this disclosure.

With continued reference to FIG. 1, physiological data may include one or more user body measurements. A "user body measurement" as used in this disclosure, includes a measurable indicator of the severity, absence, and/or presence of a disease state. A "disease state" as used in this disclosure, includes any harmful deviation from the normal structural and/or function state of a human being. A disease state may include any medical condition and may be associated with specific symptoms and signs. A disease state may be classified into different types including infectious diseases, deficiency diseases, hereditary diseases, and/or physiological diseases. For instance and without limitation, internal dysfunction of the immune system may produce a variety of different diseases including immunodeficiency, hypersensitivity, allergies, and/or autoimmune disorders.

With continued reference to FIG. 1, user body measurements may be related to particular dimensions of the human body. A "dimension of the human body" as used in this disclosure, includes one or more functional body systems that are impaired by disease in a human body and/or animal body. Functional body systems may include one or more body systems recognized as attributing to root causes of disease by functional medicine practitioners and experts. A "root cause" as used in this disclosure, includes any chain of causation describing underlying reasons for a particular disease state and/or medical condition instead of focusing solely on symptomatology reversal. Root cause may include chains of causation developed by functional medicine practices that may focus on disease causation and reversal. For instance and without limitation, a medical condition such as diabetes may include a chain of causation that does not include solely impaired sugar metabolism but that also includes impaired hormone systems including insulin resistance, high cortisol, less than optimal thyroid production, and low sex hormones. Diabetes may include further chains of causation that include inflammation, poor diet, delayed food allergies, leaky gut, oxidative stress, damage to cell membranes, and dysbiosis. Dimensions of the human body may include but are not limited to epigenetics, gut-wall, microbiome, nutrients, genetics, and/or metabolism.

With continued reference to FIG. 1, epigenetic, as used herein, includes any user body measurements describing changes to a genome that do not involve corresponding changes in nucleotide sequence. Epigenetic body measurement may include data describing any heritable phenotypic. Phenotype, as used herein, include any observable trait of a user including morphology, physical form, and structure. Phenotype may include a user's biochemical and physiological properties, behavior, and products of behavior. Behavioral phenotypes may include cognitive, personality, and behavior patterns. This may include effects on cellular and physiological phenotypic traits that may occur due to external or environmental factors. For example, DNA methylation and histone modification may alter phenotypic expression of genes without altering underlying DNA sequence. Epigenetic body measurements may include data describing one or more states of methylation of genetic material.

With continued reference to FIG. 1, gut-wall, as used herein, includes the space surrounding the lumen of the gastrointestinal tract that is composed of four layers including the mucosa, submucosa, muscular layer, and serosa. The mucosa contains the gut epithelium that is composed of goblet cells that function to secrete mucus, which aids in lubricating the passage of food throughout the digestive tract. The goblet cells also aid in protecting the intestinal wall from destruction by digestive enzymes. The mucosa includes villi or folds of the mucosa located in the small intestine that increase the surface area of the intestine. The villi contain a lacteal, that is a vessel connected to the lymph system that aids in removal of lipids and tissue fluids. Villi may contain microvilli that increase the surface area over which absorption can take place. The large intestine lack villi and instead a flat surface containing goblet cells are present.

With continued reference to FIG. 1, gut-wall includes the submucosa, which contains nerves, blood vessels, and elastic fibers containing collagen. Elastic fibers contained within the submucosa aid in stretching the gastrointestinal tract with increased capacity while also maintaining the shape of the intestine. Gut-wall includes muscular layer which contains smooth muscle that aids in peristalsis and the movement of digested material out of and along the gut. Gut-wall includes the serosa which is composed of connective tissue and coated in mucus to prevent friction damage from the intestine rubbing against other tissue. Mesenteries are also found in the serosa and suspend the intestine in the abdominal cavity to stop it from being disturbed when a person is physically active.

With continued reference to FIG. 1, gut-wall body measurement may include data describing one or more test results including results of gut-wall function, gut-wall integrity, gut-wall strength, gut-wall absorption, gut-wall permeability, intestinal absorption, gut-wall barrier function, gut-wall absorption of bacteria, gut-wall malabsorption, gut-wall gastrointestinal imbalances and the like.

With continued reference to FIG. 1, gut-wall body measurement may include any data describing blood test results of creatinine levels, lactulose levels, zonulin levels, and mannitol levels. Gut-wall body measurement may include blood test results of specific gut-wall body measurements including d-lactate, endotoxin lipopolysaccharide (LPS) Gut-wall body measurement may include data breath tests measuring lactulose, hydrogen, methane, lactose, and the like. Gut-wall body measurement may include blood test results describing blood chemistry levels of albumin, bilirubin, complete blood count, electrolytes, minerals, sodium, potassium, calcium, glucose, blood clotting factors, With continued reference to FIG. 1, gut-wall body measurement may include one or more stool test results describing presence or absence of parasites, firmicutes, Bacteroidetes, absorption, inflammation, food sensitivities. Stool test results may describe presence, absence, and/or measurement of acetate, aerobic bacterial cultures, anerobic bacterial cultures, fecal short chain fatty acids, beta-glucuronidase, cholesterol, chymotrypsin, fecal color, *cryptosporidium* EIA, *Entamoeba histolytica*, fecal lactoferrin, *Giardia lamblia* EIA, long chain fatty acids, meat fibers and vegetable fibers, mucus, occult blood, parasite identification, phospholipids, propionate, putrefactive short chain fatty acids, total fecal fat, triglycerides, yeast culture, n-butyrate, pH and the like.

With continued reference to FIG. 1, gut-wall body measurement may include one or more stool test results describing presence, absence, and/or measurement of microorganisms including bacteria, archaea, fungi, protozoa, algae, viruses, parasites, worms, and the like. Stool test results may contain species such as *Bifidobacterium* species, *campylobacter* species, *Clostridium difficile, cryptosporidium* species, *Cyclospora cayetanensis, Cryptosporidium* EIA, *Dientamoeba fragilis, Entamoeba histolytica, Escherichia coli, Entamoeba histolytica, Giardia, H. pylori, Candida albicans, Lactobacillus* species, worms, macroscopic worms, mycology, protozoa, Shiga toxin *E. coli*, and the like.

With continued reference to FIG. 1, gut-wall body measurement may include one or more microscopic ova exam results, microscopic parasite exam results, protozoan polymerase chain reaction test results and the like. Gut-wall body measurement may include enzyme-linked immunosorbent assay (ELISA) test results describing immunoglobulin G (Ig G) food antibody results, immunoglobulin E (Ig E) food antibody results, Ig E mold results, IgG spice and herb results. Gut-wall body measurement may include measurements of calprotectin, eosinophil protein x (EPX), stool weight, pancreatic elastase, total urine volume, blood creatinine levels, blood lactulose levels, blood mannitol levels.

With continued reference to FIG. 1, gut-wall body measurement may include one or more elements of data describing one or more procedures examining gut including for example colonoscopy, endoscopy, large and small molecule challenge and subsequent urinary recovery using large molecules such as lactulose, polyethylene glycol-3350, and small molecules such as mannitol, L-rhamnose, polyethyleneglycol-400. Gut-wall body measurement may include data describing one or more images such as x-ray, MRI, CT scan, ultrasound, standard barium follow-through examination, barium enema, barium with contract, MRI fluoroscopy, positron emission tomography 9PET), diffusion-weighted MM imaging, and the like.

With continued reference to FIG. 1, microbiome, as used herein, includes ecological community of commensal, symbiotic, and pathogenic microorganisms that reside on or within any of a number of human tissues and biofluids. For example, human tissues and biofluids may include the skin, mammary glands, placenta, seminal fluid, uterus, vagina, ovarian follicles, lung, saliva, oral mucosa, conjunctiva, biliary, and gastrointestinal tracts. Microbiome may include for example, bacteria, archaea, protists, fungi, and viruses. Microbiome may include commensal organisms that exist within a human being without causing harm or disease. Microbiome may include organisms that are not harmful but rather harm the human when they produce toxic metabolites such as trimethylamine. Microbiome may include pathogenic organisms that cause host damage through virulence factors such as producing toxic by-products. Microbiome may include populations of microbes such as bacteria and yeasts that may inhabit the skin and mucosal surfaces in various parts of the body. Bacteria may include for example Firmicutes species, Bacteroidetes species, Proteobacteria species, Verrumicrobia species, Actinobacteria species, Fusobacteria species, Cyanobacteria species and the like. Archaea may include methanogens such as Methanobrevibacter smithies' and Methanosphaera stadtmanae. Fungi may include *Candida* species and *Malassezia* species. Viruses may include bacteriophages. Microbiome species may vary in different locations throughout the body. For example, the genitourinary system may contain a high prevalence of *Lactobacillus* species while the gastrointestinal tract may contain a high prevalence of *Bifidobacterium* species while the lung may contain a high prevalence of *Streptococcus* and *Staphylococcus* species.

With continued reference to FIG. 1, microbiome body measurement may include one or more stool test results describing presence, absence, and/or measurement of microorganisms including bacteria, archaea, fungi, protozoa, algae, viruses, parasites, worms, and the like. Stool test results may contain species such as *Ackerman's muciniphila, Anaerotruncus colihominis,* bacteriology, *Bacteroides vulgates', Bacteroides-Prevotella, Barnesiella* species, *Bifidobacterium* longarm, *Bifidobacterium* species, *Butyrivbrio crossotus, Clostridium* species, *Collinsella aerofaciens,* fecal color, fecal consistency, *Coprococcus eutactus, Desulfovibrio piger, Escherichia coli, Faecalibacterium prausnitzii,* Fecal occult blood, Firmicutes to Bacteroidetes ratio, *Fusobacterium* species, *Lactobacillus* species, *Methanobrevibacter smithii,* yeast minimum inhibitory concentration, bacteria minimum inhibitory concentration, yeast mycology, fungi mycology, *Odoribacter* species, *Oxalobacter formigenes,* parasitology, *Prevotella* species, *Pseudoflavonifractor* species, *Roseburia* species, *Ruminococcus* species, *Veillonella* species and the like.

With continued reference to FIG. 1, microbiome body measurement may include one or more stool tests results that identify all microorganisms living a user's gut including bacteria, viruses, archaea, yeast, fungi, parasites, and bacteriophages. Microbiome body measurement may include DNA and RNA sequences from live microorganisms that may impact a user's health. Microbiome body measurement may include high resolution of both species and strains of all microorganisms. Microbiome body measurement may include data describing current microbe activity. Microbiome body measurement may include expression of levels of active microbial gene functions. Microbiome body measurement may include descriptions of sources of disease causing microorganisms, such as viruses found in the gastrointestinal tract such as raspberry bushy swarf virus from consuming contaminated raspberries or Pepino mosaic virus from consuming contaminated tomatoes.

With continued reference to FIG. 1, microbiome body measurement may include one or more blood test results that identify metabolites produced by microorganisms. Metabolites may include for example, indole-3-propionic acid, indole-3-lactic acid, indole-3-acetic acid, tryptophan, serotonin, kynurenine, total indoxyl sulfate, tyrosine, xanthine, 3-methylxanthine, uric acid, and the like.

With continued reference to FIG. 1, microbiome body measurement may include one or more breath test results that identify certain strains of microorganisms that may be present in certain areas of a user's body. This may include for example, lactose intolerance breath tests, methane-based breath tests, hydrogen based breath tests, fructose based breath tests. *Helicobacter pylori* breath test, fructose intolerance breath test, bacterial overgrowth syndrome breath tests and the like.

With continued reference to FIG. 1, microbiome body measurement may include one or more urinary analysis results for certain microbial strains present in urine. This may include for example, urinalysis that examines urine specific gravity, urine cytology, urine sodium, urine culture, urinary calcium, urinary hematuria, urinary glucose levels, urinary acidity, urinary protein, urinary nitrites, bilirubin, red blood cell urinalysis, and the like.

With continued reference to FIG. 1, nutrient as used herein, includes any substance required by the human body to function. Nutrients may include carbohydrates, protein, lipids, vitamins, minerals, antioxidants, fatty acids, amino acids, and the like. Nutrients may include for example vitamins such as thiamine, riboflavin, niacin, pantothenic acid, pyridoxine, biotin, folate, cobalamin, Vitamin C, Vitamin A, Vitamin D, Vitamin E, and Vitamin K. Nutrients may include for example minerals such as sodium, chloride, potassium, calcium, phosphorous, magnesium, sulfur, iron, zinc, iodine, selenium, copper, manganese, fluoride, chromium, molybdenum, nickel, aluminum, silicon, vanadium, arsenic, and boron.

With continued reference to FIG. 1, nutrients may include extracellular nutrients that are free floating in blood and exist outside of cells. Extracellular nutrients may be located in serum. Nutrients may include intracellular nutrients which may be absorbed by cells including white blood cells and red blood cells.

With continued reference to FIG. 1, nutrient body measurement may include one or more blood test results that identify extracellular and intracellular levels of nutrients. Nutrient body measurement may include blood test results that identify serum, white blood cell, and red blood cell levels of nutrients. For example, nutrient body measurement may include serum, white blood cell, and red blood cell levels of micronutrients such as Vitamin A, Vitamin B1, Vitamin B2, Vitamin B3, Vitamin B6, Vitamin B12, Vitamin B5, Vitamin C, Vitamin D, Vitamin E, Vitamin K1, Vitamin K2, and folate.

With continued reference to FIG. 1, nutrient body measurement may include one or more blood test results that identify serum, white blood cell and red blood cell levels of nutrients such as calcium, manganese, zinc, copper, chromium, iron, magnesium, copper to zinc ratio, choline, inositol, carnitine, methylmalonic acid (MMA), sodium, potassium, asparagine, glutamine, serine, coenzyme q10, cysteine, alpha lipoic acid, glutathione, selenium, eicosapentaenoic acid (EPA), docosahexaenoic acid (DHA), docosapentaenoic acid (DPA), total omega-3, lauric acid, arachidonic acid, oleic acid, total omega 6, and omega 3 index.

With continued reference to FIG. 1, nutrient body measurement may include one or more salivary test results that identify levels of nutrients including any of the nutrients as described herein. Nutrient body measurement may include hair analysis of levels of nutrients including any of the nutrients as described herein.

With continued reference to FIG. 1, genetic as used herein, includes any inherited trait. Inherited traits may include genetic material contained with DNA including for example, nucleotides. Nucleotides include adenine (A), cytosine (C), guanine (G), and thymine (T). Genetic information may be contained within the specific sequence of an individual's nucleotides and sequence throughout a gene or DNA chain. Genetics may include how a particular genetic sequence may contribute to a tendency to develop a certain disease such as cancer or Alzheimer's disease.

With continued reference to FIG. 1, genetic body measurement may include one or more results from one or more blood tests, hair tests, skin tests, urine, amniotic fluid, buccal swabs and/or tissue test to identify a user's particular sequence of nucleotides, genes, chromosomes, and/or proteins. Genetic body measurement may include tests that example genetic changes that may lead to genetic disorders. Genetic body measurement may detect genetic changes such as deletion of genetic material or pieces of chromosomes that may cause Duchenne Muscular Dystrophy. Genetic body measurement may detect genetic changes such as insertion of genetic material into DNA or a gene such as the BRCA1 gene that is associated with an increased risk of breast and ovarian cancer due to insertion of 2 extra nucleotides. Genetic body measurement may include a genetic change such as a genetic substitution from a piece of genetic material that replaces another as seen with sickle cell anemia where one nucleotide is substituted for another. Genetic body measurement may detect a genetic change such as a duplication when extra genetic material is duplicated one or more times within a person's genome such as with Charcot-Marie Tooth disease type 1. Genetic body measurement may include a genetic change such as an amplification when there is more than a normal number of copies of a gene in a cell such as HER2 amplification in cancer cells. Genetic body measurement may include a genetic change such as a chromosomal translocation when pieces of chromosomes break off and reattach to another chromosome such as with the BCR-ABL1 gene sequence that is formed when pieces of chromosome 9 and chromosome 22 break off and switch places. Genetic body measurement may include a genetic change such as an inversion when one chromosome experiences two breaks and the middle piece is flipped or inverted before reattaching. Genetic body measurement may include a repeat such as when regions of DNA contain a sequence of nucleotides that repeat a number of times such as for example in Huntington's disease or Fragile X syndrome. Genetic body measurement may include a genetic change such as a trisomy when there are three chromosomes instead of the usual pair as seen with Down syndrome with a trisomy of chromosome 21, Edwards syndrome with a trisomy at chromosome 18 or Patau syndrome with a trisomy at chromosome 13. Genetic body measurement may include a genetic change such as monosomy such as when there is an absence of a chromosome instead of a pair, such as in Turner syndrome.

With continued reference to FIG. 1, genetic body measurement may include an analysis of COMT gene that is responsible for producing enzymes that metabolize neurotransmitters. Genetic body measurement may include an analysis of DRD2 gene that produces dopamine receptors in the brain. Genetic body measurement may include an analysis of ADRA2B gene that produces receptors for noradrenaline. Genetic body measurement may include an analysis of 5-HTTLPR gene that produces receptors for serotonin. Genetic body measurement may include an analysis of BDNF gene that produces brain derived neurotrophic factor. Genetic body measurement may include an analysis of 9p21 gene that is associated with cardiovascular disease risk. Genetic body measurement may include an analysis of APOE gene that is involved in the transportation of blood lipids such as cholesterol. Genetic body measurement may include an analysis of NOS3 gene that is involved in producing enzymes involved in regulating vaso-dilation and vaso-constriction of blood vessels.

With continued reference to FIG. 1, genetic body measurement may include ACE gene that is involved in producing enzymes that regulate blood pressure. Genetic body measurement may include SLCO1B1 gene that directs pharmaceutical compounds such as statins into cells. Genetic body measurement may include FUT2 gene that produces enzymes that aid in absorption of Vitamin B12 from digestive tract. Genetic body measurement may include MTHFR gene that is responsible for producing enzymes that aid in metabolism and utilization of Vitamin B9 or folate. Genetic body measurement may include SHMT1 gene that aids in production and utilization of Vitamin B9 or folate. Genetic body measurement may include MTRR gene that produces enzymes that aid in metabolism and utilization of Vitamin B12. Genetic body measurement may include MTR gene that produces enzymes that aid in metabolism and utilization of Vitamin B12. Genetic body measurement may include FTO gene that aids in feelings of satiety or fulness after eating. Genetic body measurement may include MC4R gene that aids in producing hunger cues and hunger triggers. Genetic body measurement may include APOA2 gene that directs body to produce ApoA2 thereby affecting absorption of saturated fats. Genetic body measurement may include UCP1 gene that aids in controlling metabolic rate and thermoregulation of body. Genetic body measurement may include TCF7L2 gene that regulates insulin secretion. Genetic body measurement may include AMY1 gene that aids in digestion of starchy foods. Genetic body measurement may include MCM6 gene that controls production of lactase enzyme that aids in digesting lactose found in dairy products. Genetic body measurement may include BCMO1 gene that aids in producing enzymes that aid in metabolism and activation of Vitamin A. Genetic body measurement may include SLC23A1 gene that produce and transport Vitamin C. Genetic body measurement may include CYP2R1 gene that produce enzymes involved in production and activation of Vitamin D. Genetic body measurement may include GC gene that produce and transport Vitamin D. Genetic body measurement may include CYP1A2 gene that aid in metabolism and elimination of caffeine. Genetic body measurement may include CYP17A1 gene that produce enzymes that convert progesterone into androgens such as androstenedione, androstendiol, dehydroepiandrosterone, and testosterone.

With continued reference to FIG. 1, genetic body measurement may include CYP19A1 gene that produce enzymes that convert androgens such as androstenedione and testosterone into estrogens including estradiol and estrone. Genetic body measurement may include SRD5A2 gene that aids in production of enzymes that convert testosterone into dihydrotestosterone. Genetic body measurement may include UFT2B17 gene that produces enzymes that metabolize testosterone and dihydrotestosterone. Genetic body measurement may include CYP1A1 gene that produces enzymes that metabolize estrogens into 2 hydroxy-estrogen. Genetic body measurement may include CYP1B1 gene that produces enzymes that metabolize estrogens into 4 hydroxy-estrogen. Genetic body measurement may include CYP3A4 gene that produces enzymes that metabolize estrogen into 16 hydroxy-estrogen. Genetic body measurement may include COMT gene that produces enzymes that metabolize 2 hydroxy-estrogen and 4 hydroxy-estrogen into methoxy estrogen. Genetic body measurement may include GSTT1 gene that produces enzymes that eliminate toxic by-products generated from metabolism of estrogens. Genetic body measurement may include GSTM1 gene that produces enzymes responsible for eliminating harmful by-products generated from metabolism of estrogens. Genetic body measurement may include GSTP1 gene that produces enzymes that eliminate harmful by-products generated from metabolism of estrogens. Genetic body measurement may include SOD2 gene that produces enzymes that eliminate oxidant by-products generated from metabolism of estrogens.

With continued reference to FIG. 1, metabolic, as used herein, includes any process that converts food and nutrition into energy. Metabolic may include biochemical processes that occur within the body. Metabolic body measurement may include blood tests, hair tests, skin tests, amniotic fluid, buccal swabs and/or tissue test to identify a user's metabolism. Metabolic body measurement may include blood tests that examine glucose levels, electrolytes, fluid balance, kidney function, and liver function. Metabolic body measurement may include blood tests that examine calcium levels, albumin, total protein, chloride levels, sodium levels, potassium levels, carbon dioxide levels, bicarbonate levels, blood urea nitrogen, creatinine, alkaline phosphatase, alanine amino transferase, aspartate amino transferase, bilirubin, and the like.

With continued reference to FIG. 1, metabolic body measurement may include one or more blood, saliva, hair, urine, skin, and/or buccal swabs that examine levels of hormones within the body such as 11-hydroxy-androstereone, 11-hydroxy-etiocholanolone, 11-keto-androsterone, 11-keto-etiocholanolone, 16 alpha-hydroxyestrone, 2-hydroxyestrone, 4-hydroxyestrone, 4-methoxyestrone, androstanediol, androsterone, creatinine, DHEA, estradiol, estriol, estrone, etiocholanolone, pregnanediol, pregnanestriol, specific gravity, testosterone, tetrahydrocortisol, tetrahydrocrotisone, tetrahydrodeoxycortisol, allo-tetrahydrocortisol.

With continued reference to FIG. 1, metabolic body measurement may include one or more metabolic rate test results such as breath tests that may analyze a user's resting metabolic rate or number of calories that a user's body burns each day rest. Metabolic body measurement may include one or more vital signs including blood pressure, breathing rate, pulse rate, temperature, and the like. Metabolic body measurement may include blood tests such as a lipid panel such as low density lipoprotein (LDL), high density lipoprotein (HDL), triglycerides, total cholesterol, ratios of lipid levels such as total cholesterol to HDL ratio, insulin sensitivity test, fasting glucose test, Hemoglobin A1C test, adipokines such as leptin and adiponectin, neuropeptides such as ghrelin, pro-inflammatory cytokines such as interleukin 6 or tumor necrosis factor alpha, anti-inflammatory cytokines such as interleukin 10, markers of antioxidant status such as oxidized low-density lipoprotein, uric acid, paraoxonase 1. Persons skilled in the art, upon reviewing the entirety of this disclosure, will be aware of various additional examples of physiological state data that may be used consistently with descriptions of systems and methods as provided in this disclosure.

With continued reference to FIG. 1, physiological data may be obtained from a physically extracted sample. A "physical sample" as used in this example, may include any sample obtained from a human body of a user. A physical sample may be obtained from a bodily fluid and/or tissue analysis such as a blood sample, tissue, sample, buccal swab, mucous sample, stool sample, hair sample, fingernail sample and the like. A physical sample may be obtained from a device in contact with a human body of a user such as a microchip embedded in a user's skin, a sensor in contact with a user's skin, a sensor located on a user's tooth, and the like. Physiological data may be obtained from a physically extracted sample. A physical sample may include a signal from a sensor configured to detect physiological data of a user and record physiological data as a function of the signal. A sensor may include any medical sensor and/or medical device configured to capture sensor data concerning a patient, including any scanning, radiological and/or imaging device such as without limitation x-ray equipment, computer assisted tomography (CAT) scan equipment, positron emission tomography (PET) scan equipment, any form of magnetic resonance imagery (MRI) equipment, ultrasound equipment, optical scanning equipment such as photo-plethysmographic equipment, or the like. A sensor may include any electromagnetic sensor, including without limitation electroencephalographic sensors, magnetoencephalographic sensors, electrocardiographic sensors, electromyographic sensors, or the like. A sensor may include a temperature sensor. A sensor may include any sensor that may be included in a mobile device and/or wearable device, including without limitation a motion sensor such as an inertial measurement unit (IMU), one or more accelerometers, one or more gyroscopes, one or more magnetometers, or the like. At least a wearable and/or mobile device sensor may capture step, gait, and/or other mobility data, as well as data describing activity levels and/or physical fitness. At least a wearable and/or mobile device sensor may detect heart rate or the like. A sensor may detect any hematological parameter including blood oxygen level, pulse rate, heart rate, pulse rhythm, blood sugar, and/or blood pressure. A sensor may be configured to detect internal and/or external biomarkers and/or readings. A sensor may be a part of system 100 or may be a separate device in communication with system 100.

With continued reference to FIG. 1, computing device 104 may retrieve a biological extraction 116 from a biological extraction database 120. Biological extraction database 120 may be implemented, without limitation, as a relational database, a key-value retrieval datastore such as a NOSQL database, or any other form or structure for use as a datastore that a person skilled in the art would recognize as suitable upon review of the entirety of this disclosure. Biological extraction database 120 may include one or more elements of data pertaining to a user including a conditional datum 112, as described below in more detail.

With continued reference to FIG. 1, computing device 104 is configured to receive conditional training data 124. "Conditional training data," as used in this disclosure, is training data that contains a plurality of biological extraction 116 and a plurality of correlated conditions. "Training data," as used in this disclosure, is data containing correlations that a machine-learning process may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate causative and/or predictive links between categories of data elements, which may be modeled as relationships such as mathematical relationships by machine-learning processes as described in further detail below. Training data may be formatted and/or organized by categories of data elements, for instance by associating data elements with one or more descriptors corresponding to categories of data elements. As a non-limiting example, training data may include data entered in standardized forms by persons or processes, such that entry of a given data element in a given field in a form may be mapped to one or more descriptors of categories. Elements in training data may be linked to descriptors of categories by tags, tokens, or other data elements; for instance, and without limitation, training data may be provided in fixed-length formats, formats linking positions of data to categories such as comma-separated value (CSV) formats and/or self-describing formats such as extensible markup language (XML), enabling processes or devices to detect categories of data.

Alternatively or additionally, and still referring to FIG. 1, training data may include one or more elements that are not categorized; that is, training data may not be formatted or contain descriptors for some elements of data. Machine-learning algorithms and/or other processes may sort training data according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data to be made applicable for two or more distinct machine-learning algorithms as described in further detail below. Training data used by computing device 104 may correlate any input data as described in this disclosure to any output data as described in this disclosure.

With continued reference to FIG. 1, computing device 104 is configured to generate a conditional model 128. A "conditional model," as used in this disclosure, is a machine-learning model that utilizes a biological extraction 116 as an input and outputs a conditional datum 112 containing a suspected condition. A machine-learning model, as used herein, is a mathematical representation of a relationship between inputs and outputs, as generated using any machine-learning process including without limitation any process as described above, and stored in memory; an input is submitted to a machine-learning model once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model may be generated by creating an artificial neural network, such as a convolutional neural network comprising an input layer of nodes, one or more intermediate layers, and an output layer of nodes. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

With continued reference to FIG. 1, a machine-learning process, also referred to as a machine-learning algorithm, is a process that automatedly uses training data and/or a training set as described above to generate an algorithm that will be performed by a computing device 104 and/or module to produce outputs given data provided as inputs; this is in contrast to a non-machine-learning software program where the commands to be executed are determined in advance by a user and written in a programming language.

Continuing to refer to FIG. 1, machine-learning algorithms may be implemented using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure, Still referring to FIG. 1, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

With continued reference to FIG. 1, models may be generated using alternative or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using training data.

Still referring to FIG. 1, machine-learning algorithms may include supervised machine-learning algorithms. Supervised machine-learning algorithms, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised machine-learning process may include a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data. Persons skilled in the art, upon reviewing the entirety of this disclosure, will be aware of various possible variations of supervised machine-learning algorithms that may be used to determine relation between inputs and outputs.

With continued reference to FIG. 1, supervised machine-learning processes may include classification algorithms, defined as processes whereby a computing device 104 derives, from training data, a model for sorting inputs into categories or bins of data. Classification may be performed using, without limitation, linear classifiers such as without limitation logistic regression and/or naive Bayes classifiers, nearest neighbor classifiers including without limitation k-nearest neighbors classifiers, support vector machines, decision trees, boosted trees, random forest classifiers, and/or neural network-based classifiers.

Still referring to FIG. 1, machine-learning processes may include unsupervised processes. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like. Unsupervised machine-learning algorithms may include, without limitation, clustering algorithms and/or cluster analysis processes, such as without limitation hierarchical clustering, centroid clustering, distribution clustering, clustering using density models, subspace models, group models, graph-based models, signed graph models, neural models, or the like. Unsupervised learning may be performed by neural networks and/or deep learning protocols as described above.

With continued reference to FIG. 1, a "suspected condition," as used in this disclosure, is data describing any likely diagnosis. A likely diagnosis may indicate a diagnosis that is qualified as being probable, still needs to be ruled out, and/or may need to be reviewed by an informed advisor.

With continued reference to FIG. 1, computing device 104 is configured to identify a plurality of antidotal therapeutic provisions 132. An "antidotal therapeutic provision," as used in this disclosure, is any health care material, product, and/or device prescribed and/or recommended by an informed advisor, used to serve a medical purpose. An antidotal therapeutic provision may include a medical device, a piece of medical equipment, a medical apparatus, a medical material, a medical product, a medical instrument, and the like. An antidotal therapeutic provision may include any ostomy supplies, catheter, oxygen, diabetic supplies and the like. An antidotal therapeutic provision may include any durable medical equipment including crutches, hospital beds, infusion pumps, infusion supplies, wheelchairs, nebulizers, nebulizer medications, blood sugar monitors, blood sugar test strips, diabetic socks, canes, commode chairs, continuous passive motion devices, continuous positive airway pressure (CPAP) devices, lancet devices, lancets, oxygen equipment, oxygen accessories, patient lifts, pressure-reducing beds, mattresses, mattress overlays, suction cups, traction equipment, walkers, scooters and the like. An antidotal therapeutic provision may include any home health supplies including assistive furniture, bath safety, walking aids, incontinence products, wound care products, urological products, orthopedic products, skin care, respiratory products and the like. For instance and without limitation, an antidotal therapeutic provision may include under pads, adult briefs, pullup underwear, washcloths and wipes, power wheelchair, transport wheelchair, manual wheelchair, adhesive tape, bandages, medicated wound dressing, gauze sponges, urinals, bedpans, leg bags, external catheters, foley catheters, skin barriers, pouches, irrigation systems, ostomy accessories, arm slings, back and abdominal supports, joint support intended for foot, ankle, elbow, and wrist, wrist and/or thumb support and braces, anti-bacterial products, anti-fungal products, barrier products, creams, lotions, and powders, protective wear, tracheal care, compressors, nebulizers, oxygen masks, cannulas, oxygen tank cylinders, electrotherapy, hot and cold therapy, defibrillators, defibrillator pads, defibrillator cabinets, and the like. An antidotal therapeutic provision may include a medical device. A medical device may include any instrument, apparatus, implant, machine, appliance, in vitro reagent, software, material and/or other similar or related article that may be utilized in the diagnosis, prevention, monitoring, treatment, and/or alleviation of a disease. A medical device may include any device intended to be used for a medical purpose. A medical device may be recognized in the official National Formulary, or the U.S. Pharmacopoeia. A medical device may be intended to affect the structure or any function of the body of man or other animals. For instance and without limitation, a medical device may include but is not limited to, an inflatable extremity splint, an oxygen mask, a line isolation monitor, an intra-oral dental drill, a powered toothbrush, a nebulizer, a cardiac monitor, a hemodialysis system, an electro-surgical cutting and coagulation device, a surgical laser for dermatology use, a cardiovascular stent, an intra-aortic balloon, an implanted urinary continence device, an implantable diaphragmatic and phrenic nerve stimulator, a membrane lung for long term pulmonary support.

With continued reference to FIG. 1, computing device 104 identifies a plurality of antidotal therapeutic provision 132 using a therapeutic clustering model 136. A "therapeutic clustering model," as used in this disclosure, is a machine-learning model that utilizes a conditional datum 112 as an input and outputs antidotal therapeutic provision 132. Therapeutic clustering model 136 may be generated utilizing one or more clustering algorithms. A "clustering algorithm," as used in this disclosure, is a series of one or more calculations that groups a set of objects in such a way that objects in the same group or cluster are more similar to each other than to those in other groups or clusters. A clustering algorithm may include generating one or more clustering models. Clustering models may include for example, connectivity models such as hierarchical clustering. Clustering models may include for example, centroid models such as k-means algorithm. Clustering models may include for example, distribution models such as multivariate normal distributions using an expectation-maximization algorithm. Clustering models may include for example, density models such as density-based spatial clustering of applications with noise (DBSCAN) or ordering points to identify a clustering structure (OPTICS). Clustering models may include for example, subspace models such as bi-clustering. Clustering models may include for example, group models. Clustering models may include graph-based models such as highly connected subgraphs (HCS) clustering algorithm. Clustering models may include signed graph models. Clustering models may include neural models such as an unsupervised neural network With continued reference to FIG. 1, clustering algorithms and/or clustering models may be generated as hard and/or soft clusters. Clustering algorithms and/or clustering models may include hard clusters whereby each object belongs to a cluster or not. Clustering algorithms and/or clustering models may include soft clustering whereby each object may belong to each cluster to a certain degree. Clustering algorithms and/or clustering models may include strict partitioning clustering where each object belongs to exactly one cluster. Clustering algorithms and/or clustering models may include strict partitioning clustering with outliers where objects can also belong to no cluster and may be considered outliers. Clustering algorithms and/or clustering models may include overlapping clustering where objects may belong to more than one cluster. Clustering algorithms and/or clustering models may include hierarchical clustering where objects that belong to a child cluster may also belong to the parent cluster. Clustering algorithms and/or clustering models may include subspace clustering.

With continued reference to FIG. 1, computing device 104 generates therapeutic clustering model 136 utilizing a clustering dataset 140. A "clustering dataset," as used in this disclosure, includes a plurality of unclassified cluster data entries. An "unclassified cluster data entry," as used in this disclosure, is a data entry that has not been assigned, generated, and/or calculated a category label. Cluster data entries may become classified cluster data entries through classification. Classification may include using predictive modeling to approximate a mapping function from input variables to discrete output variables. Classification may be performed utilizing classification algorithms that include for example, decision trees, naïve Bayes, artificial neural networks, boosting, kernel methods, and/or k-nearest neighbors algorithm.

With continued reference to FIG. 1, computing device 104 generates therapeutic clustering model 136 by calculating a first clustering algorithm. First clustering algorithm includes any of the clustering algorithms as described above. First clustering algorithm may include generating a k-means clustering algorithm. Generating a K-means clustering algorithm includes assigning inputs containing unclassified data to a "k-group" or "k-cluster" based on feature similarity. Centroids of k-groups or k-clusters may be utilized to generate classified data entry clusters. Computing device 104 selects "k" variable by calculating k-means clustering algorithm for a range of k values and comparing results.

Computing device 104 may compare results across different values of k as the mean distance between cluster data entries and cluster centroid. Computing device 104 may calculate mean distance to a centroid as a function of k value, and the location of where the rate of decrease starts to sharply shift, this may be utilized to select a k value. Centroids of k-groups or k-cluster include a collection of feature values which are utilized to classify data entry clusters containing cluster data entries. Computing device 104 may select a k value based on one or more expert inputs that may be stored within an expert database 144. Expert database 144 may be implemented as any data structure suitable for use as biological extraction database 120. For instance and without limitation, a conditional datum 112 related to ulcerative colitis may be best suited for a k-value of 77 while a conditional datum 112 related to mold toxicity may be best suited for a k-value of 14.

With continued reference to FIG. 1, generating a k-means clustering algorithm includes generating initial estimates for k centroids which may be randomly generated or randomly selected from unclassified data input. K centroids may be utilized to define one or more clusters. Computing device 104 may assign unclassified data to one or more k-centroids based on the squared Euclidean distance by first performing a data assigned step of unclassified data. Computing device 104 may assign unclassified data to its nearest centroid based on the collection of centroids $c_i$ of centroids in set C. Unclassified data may be assigned to a cluster based on $\operatorname{argmin}_{(c_i \in C)} \operatorname{dist}(c_i, x)^2$, where argmin includes argument of the minimum; $c_i$ includes a collection of centroids in a set C; and dist. includes standard Euclidean distance. Computing device 104 may then recompute centroids by taking mean of all cluster data entries assigned to a centroid's cluster. This may be calculated based on $c_i = 1/|S_i| \Sigma_{x_i \in S_i} (x_i)$. Computing device 104 may continue to repeat these calculations until a stopping criterion has been satisfied such as when cluster data entries do not change clusters, the sum of the distances have been minimized, and/or some maximum number of iterations has been reached.

With continued reference to FIG. 1, computing device 104 may generate a first clustering algorithm that includes a hierarchical clustering algorithm. Hierarchical clustering includes any clustering algorithm that seeks to generate a hierarchy of clusters. Hierarchical clustering includes agglomerative clustering where each observation starts in its own cluster and pairs of clusters are merged as one moves up the hierarchy. Hierarchical clustering includes divisive clustering where each observation starts in one cluster and splits are performed recursively as one moves down the hierarchy. Generating hierarchical clustering algorithm may include measuring dissimilarity between sets of observations. This may include measuring distance between pairs of observations utilizing an appropriate metric. Distance between pairs of observations may be measured utilizing for example, Euclidean distance, squared Euclidean distance, Manhattan distance, Maximum distance, Hamming distance, levenshtein distance, and/or Mahalanobis distance. Generating hierarchical clustering algorithm may include measuring a linkage criterion between observations which specifies the dissimilarity of sets as a function of pairwise distances of observations in sets. Linkage criterion may be measured utilizing maximum or complete-linkage clustering, minimum or single-linkage clustering, unweighted average linkage clustering (UPGMA), weighted average linkage clustering (WPGMA), centroid linkage clustering (UPGMC), and/or minimum energy clustering.

With continued reference to FIG. 1, computing device 104 is configured to calculate a user effective age 148. A "user effective age," as used in this disclosure, is an age of a user as adjusted to reflect a life expectancy that differs from an actuarially projected life expectancy. For instance, a user effective age 148 of a person predicted to live fewer years than actuarially projected may be higher than a user effective age 148 of a person predicted to match and/or exceed an actuarially projected life expectancy. User effective age 148 may be used as a representation of a user's likely overall state of health, inasmuch as a user's likelihood to exceed or fall short of actuarially projected life expectancy may be closely linked to a user's state of health. A user's "chronological age," as defined in this disclosure, is an age of the user as measured in years, or other units of time, from the date of the user's birth to the date of the measurement, where a "date" may include any calendar date, Julian date, or the like. A chronological age may be used to project a user's "actuarial life expectancy," defined as a probable age of death, as predicted using any actuarial method and/or table, and/or an interval from a date such as the present date to the probable age of death; actuarial methods may include looking up and/or calculating a user's life expectancy using date of birth and/or demographic information about the user such as sex, ethnicity, geographic location, nationality, or the like. A user effective age 148 may be calculated based on a user's chronological age and a user's biological extraction 116. For instance and without limitation, computing device 104 may add several years to a user's chronological age to output an effective age that is older than a user's chronological age when a user's biological extraction 116 contains abnormal findings or a laboratory finding that is outside of normal limits. In yet another non-limiting example, computing device 104 may subtract several years to a user's chronological age to output an effective age that is younger than a user's chronological age when a user's biological extraction 116 contains normal findings or a laboratory finding that is within and/or below normally accepted limits.

With continued reference to FIG. 1, user effective age 148 may be calculated by multiplying a telomer length factor by an endocrinal factor multiplied by a histone variance factor to produce a positive effective age score. A "telomer length factor," as used in this disclosure, is a factor that may be multiplied by a user's chronological age to reflect an effect that telomeric length and/or a change in telomere length has on the user's effective age. Calculation may include prediction of a variance from actuarial life expectancy for a given person, as defined above, as determined based on telomeric length and/or variation in telomere length. A difference between these two values may be added to a user chronological age and then divided by the user chronological age to calculate a "raw" factor, for instance as described above; this may then be multiplied by a weight to determine the telomer length factor, whereas above the weight may be calculated to offset relatedness between telomere length and/or change in telomere length and other elements used to calculate age factors as described herein, such as endocrinal age factors. A computing device 104 may determine telomer length factor by retrieving telomer length factor from an expert database 144. Expert database 144 may be implemented, without limitation, as a relational database, a key-value retrieval datastore such as a NOSQL database, or any other form or structure for use as a datastore that a person skilled in the art would recognize as suitable upon review of the entirety of this disclosure. For instance, and without limitation, one or more experts may enter data in expert database 144 indicative of an effect on user life expectancy; such data may, for instance, be entered as described in further detail below.

With continued reference to FIG. 1, an "endocrinal factor," as used in this disclosure, is a factor that may be multiplied by a user's chronological age to reflect an effect that endocrinal data has on the user's effective age. Endocrinal data may include any physiological data relating to the endocrine system. The endocrine system includes glands that include the pineal gland, the thyroid gland, the parathyroid gland, the pituitary gland, the adrenal gland, the pancreas, the ovaries, and the testis. Endocrinal data may include one or more measurements of function of the endocrine system such as for example, a measurement of thyroid stimulating hormone (TSH) or a fasting serum insulin level. Calculation of an endocrinal factor may include any calculation for telomer length factor as described above.

With continued reference to FIG. 1, a "histone variance factor," as used in this disclosure, is a factor that may be multiplied by a user's chronological age to reflect an effect that loss of histones has on the user's effective age. Histones include alkaline proteins found in cell nuclei that package and order DNA into nucleosomes. Histones are the primary component of chromatin, maintaining a role in gene regulation. Histone loss may be linked with cell division, as reduced synthesis of new histones has been seen to be corelated with shortened telomeres that activate a DNA damage response. Loss of core histones include H2A, H2B, H3, and H4 may be considered an epigenetic mark of aging. Calculation of a histone variance factor may include any calculation for telomer length factor as described above.

With continued reference to FIG. 1, computing device 104 multiplies a telomer length factor by an endocrinal factor multiplied by a histone variance factor to produce a positive effective age score. A "positive effective age score," as used in this disclosure, is a score that results from positive influences that tend to extend life expectancy. In an embodiment, positive influences may aid in lowering an effective age to be lower than a user's chronological age. Computing device 104 adds a user behavior pattern and a user danger profile to produce a negative effective age score. A user behavior pattern and a user danger profile are described below in more detail. A "negative effective age score," as used in this disclosure, is a score that results from negative influences that tend to reduce life expectancy. In an embodiment, negative influences may result in an effective age being older than a user's chronological age. Computing device 104 adjusts a user chronological age to produce a user effective age 148 utilizing a positive effective age score and a negative effective age score. In an embodiment, computing device 104 may utilize a positive effective age score to lower a user's effective age in comparison to a user's chronological age and utilize a negative effective age score to raise a user's effective age in comparison to a user's chronological age.

With continued reference to FIG. 1, computing device 104 is configured to identify a plurality of anecdotal therapeutic provisions utilizing a user effective age 148. Computing device 104 is configured to analyze output antidotal therapeutic provisions based on a user's effective age. Computing device 104 may analyze output antidotal therapeutic provision 132 to determine if any of the output antidotal therapeutic provision 132 are suitable based on the user's effective age. Computing device 104 may analyze output antidotal therapeutic provision 132 in combination with a user's conditional datum 112. This may be performed utilizing one or more inputs contained expert database 144. For instance and without limitation, computing device 104 may evaluate an antidotal therapeutic provision that contains a large screen glucometer with large font textual displays for a user who has a user effective age 148 that indicates the user is much younger than the user's chronological age of forty five and who does not have a conditional datum 112 that relates to having any eyesight problems. In such an instance, computing device 104 may eliminate the large screen glucometer from within the plurality of antidotal therapeutic provision 132. In yet another non-limiting example, computing device 104 may evaluate an antidotal therapeutic provision 132 that contains an infusion pump that does not screen for potential drug interactions for a user who's effective age makes them much older than the user's chronological age of seventy, and as such computing device 104 may eliminate the infusion pump that does not screen for potential drug interactions based on the user's advanced effective age and the greater likelihood that the user is on multiple medications that would need to be screened for drug interactions.

With continued reference to FIG. 1, computing device 104 is configured to locate a user biological extraction 116. A biological extraction 116 includes any of the biological extraction 116 as described herein. A biological extraction 116 includes at least an element of user physiological data. Physiological data includes any of the physiological data as described above. Computing device 104 locates a user biological extraction 116 that relates to a conditional datum 112. A biological extraction 116 relates to a conditional datum 112 when the biological extraction 116 may be indicative of the conditional datum 112, when the biological extraction 116 may be utilized to monitor the status and/or the progression of the conditional datum 112, when the biological extraction 116 is utilized to plan a treatment for the conditional datum 112, when the biological extraction 116 is utilized to check for certain co-morbid and/or co-existing conditional datum 112 and the like. Computing device 104 may know that a biological extraction 116 relates to a conditional datum 112 based on one or more expert inputs contained within expert database 144.

With continued reference to FIG. 1, computing device 104 may located a biological extraction 116 related to a conditional datum 112 utilizing one or more classification algorithms. Computing device 104 may input a conditional datum 112 to a biological classifier 152. A "classifier," as used in this disclosure, is a machine-learning model, such as a mathematical model, neural net, or program generated by a machine-learning algorithm known as a classification algorithm, that sorts inputs into categories or bins of data, outputting the categories or bins of data and/or labels associated therewith. A "biological classifier," as used in this disclosure, is a classifier configured to input a conditional datum 112 and output related biological extraction 116. Biological classifier 152 may be generated using a classification algorithm, defined as a process whereby a computing device 104 derives a classifier from training data. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. Training data includes any of the training data as described above. Computing device 104 generates biological classifier 152 to locate a biological extraction 116 related to a conditional datum 112 and generate a compatibility model 156 utilizes the biological extraction 116 related to the conditional datum 112.

With continued reference to FIG. 1, computing device 104 is configured to generate a compatibility model 156. A "compatibility model," as used in this disclosure, is a machine-learning model that utilizes antidotal therapeutic provision 132 and the user biological extraction 116 as inputs and outputs compatible antidotal therapeutic provision 160. A "compatible antidotal therapeutic provision 160," as used in this disclosure, is any antidotal therapeutic provision 132 that is proper to be used based on both a user's biological extraction 116 and a user's conditional datum 112. A compatible antidotal therapeutic provision 160 is proper to be used with a user's biological extraction 116 when it will not cause harm to the user's body. A compatible antidotal therapeutic provision 160 is proper to be used with a user's conditional datum 112 when it safe and/or appropriate to be used based on a user's conditional datum 112. A compatible antidotal therapeutic provision 160 is safe and/or appropriate to be used when it would generally be acceptable to be utilized to treat, diagnose, monitor, prevent, cure, mitigate, slow down, and/or mitigate a conditional datum 112. For instance and without limitation, a compatible antidotal therapeutic provision 160 such as a patient controlled analgesia (PCA) pump may be utilized to mitigate pain caused by bone cancer. In yet another non-limiting example, a compatible antidotal therapeutic provision 160 such as blood testing strips may be used to monitor a conditional datum 112 such as gestational diabetes. A compatible antidotal therapeutic provision 160 may be considered proper to be used based on both a user's biological extraction 116 and a user's conditional datum 112 based on one or more expert inputs contained within expert database 144.

With continued reference to FIG. 1, computing device 104 is configured to generate compatibility model 156 using compatibility training data 164. "Compatibility training data," as used in this disclosure, is training data that contains a plurality of therapeutic provisions and biological extraction 116 as inputs and outputs compatible antidotal therapeutic provision 160. Computing device 104 is configured to calculate a compatibility model 156 using a first machine-learning algorithm. First machine-learning algorithm includes any of the machine-learning algorithms as described above. For instance and without limitation, first machine-learning algorithm may include a supervised machine-learning algorithm. In yet another non-limiting example, first machine-learning algorithm may include an unsupervised machine-learning algorithm.

With continued reference to FIG. 1, computing device 104 is configured to retrieve a factor related to an antidotal therapeutic provision 132. An "factor," as used in this disclosure, is data describing any variable that may be utilized to generate compatibility model 156 and output compatible antidotal therapeutic provision 160. One or more factor 168 may be stored in factor database 172, which may be implemented as any data structure suitable for use as biological extraction database 120. Computing device 104 may receive one or more factor 168 from remote device 108. In an embodiment, one or more factor 168 may be received from a remote device 108 operated by a user. In an embodiment, one or more factor 168 may be received from a remote device 108 operated by an informed advisor. Factor 168 relate to an antidotal therapeutic provision 132. A factor 168 may relate to an antidotal therapeutic provision 132 when the factor 168 concerns any factor 168 that may affect output compatible antidotal therapeutic provision 160. A factor 168 may describe any previous purchase history of any antidotal therapeutic provision 132. A factor 168 may describe the durability of any antidotal therapeutic provision 132. For example, a factor 168 may detail that an antidotal therapeutic provision 132 may be a temporary solution to a conditional datum 112 or may indicate that an antidotal therapeutic provision 132 is a long term indefinite solution to a conditional datum 112. A factor 168 may describe a variable such as cost, and how much money a user is willing to spend or budget for an antidotal therapeutic provision 132. A factor 168 may describe a variable such as an informed advisor's preference for a particular brand, manufacturer, producer, and/or product type of an antidotal therapeutic provision 132. A factor 168 may describe ease of use, such as how easy it will be for a user to adapt and utilize a particular antidotal therapeutic provision 132. A factor 168 may describe if an antidotal therapeutic provision 132 is a temporary fix or if it will be a permanent solution and/or cure for a conditional datum 112. Computing device 104 utilizes a factor 168 related to an antidotal therapeutic provision 132 to generate a compatibility model 156 utilizing the factor 168. Computing device 104 may utilize a factor 168 as an additional input to compatibility model 156. Computing device 104 outputs compatible antidotal therapeutic provision 160 utilizing the factor 168.

With continued reference to FIG. 1, computing device 104 may utilize one or more factor 168 contained within factor database 172 to generate one or more additional machine-learning algorithms. Additional machine-learning algorithms include any of the machine-learning algorithms as described above. An additional machine-learning algorithm may include a loss function, where a loss function is an expression of an output of which an optimization algorithm minimizes to generate an optimal result. As a non-limiting example, computing device 104 may retrieve one or more factor 168 from factor database 172, and calculate an output of mathematical expression using the factor 168, and output a plurality of compatible antidotal therapeutic provision 160 utilizing the variables, to produce an output having the lowest size, according to a given definition of "size," of the set of outputs representing each of the plurality of compatible antidotal therapeutic provision 160. Size may, for instance, include absolute value, numerical size or the like. Selection of different loss functions may result in identification of different compatible antidotal therapeutic provisions as generating minimal outputs; for instance where cost is associated in a first loss function with a large coefficient or weight, a factor 168 such as ease of use may minimize the first loss function, whereas a second loss function where cost has a smaller coefficient but degree of variance from ease of use which has a larger coefficient may produce a minimal output for a different compatible antidotal therapeutic provision 160.

Alternatively or additionally, and still referring to FIG. 1, each compatible antidotal therapeutic provision 160 may be represented by a mathematical expression having the same form as mathematical expression; computing device 104 may compare the former to the latter using an error function representing average difference between the two mathematical expressions. Error function may, as a non-limiting example, be calculated using the average difference between coefficients corresponding to each variable. An alimentary instruction set having a mathematical expression minimizing the error function may be selected, as representing an optimal expression of relative importance of factor 168 to a system or user. In an embodiment, error function and loss function calculations may be combined; for instance, a compatible antidotal therapeutic provision 160 resulting in a minimal aggregate expression of error function and loss function, such as a simple addition, arithmetic mean, or the like of the error function with the loss function, may be selected, corresponding to an option that minimizes total variance from optimal factor 168 while simultaneously minimizing a degree of variance from a set of priorities corresponding to other factor 168. Coefficients of mathematical expression and/or loss function may be scaled and/or normalized; this may permit comparison and/or error function calculation to be performed without skewing by varied absolute quantities of numbers.

Still referring to FIG. 1, mathematical expression and/or loss function may be provided by receiving one or more user commands. For instance, and without limitation, a graphical user interface 176 may be provided to user with a set of sliders or other user inputs permitting a user to indicate relative and/or absolute importance of each factor to the user. Sliders or other inputs may be initialized prior to user entry as equal or may be set to default values based on results of any machine-learning processes or combinations thereof as described in further detail below.

With continued reference to FIG. 1, mathematical expression and/or loss function may be generated using a machine-learning to produce loss function: i.e., regression. Mathematical expression and/or loss function be user-specific, using a training set composed of past user selections; may be updated continuously. Mathematical expression and/or loss function may initially be seeded using one or more user entries as above. User may enter a new command changing mathematical expression, and then subsequent user selections may be used to generate a new training set to modify the new expression.

With continued reference to FIG. 1, mathematical expression and/or loss function may be generated using machine-learning using a multi-user training set. Training set may be created using data of a cohort of persons having similar demographic, religious, health, and/or lifestyle characteristics to user. This may alternatively or additionally be used to seed a mathematical expression and/or loss function for a user, which may be modified by further machine-learning and/or regression using subsequent user selections of alimentary provision options.

With continued reference to FIG. 1, computing device 104 may generate a loss function of user specific factors and minimize the loss function. Computing device 104 may generate one or more compatible antidotal therapeutic provision 160 utilizing loss function analysis. Loss function analysis may measure changes in predicted values versus actual values, known as loss or error. Loss function analysis may utilize gradient descent to learn the gradient or direction that a cost analysis should take in order to reduce errors. Loss function analysis algorithms may iterate to gradually converge towards a minimum where further tweaks to the parameters produce little or zero changes in the loss or convergence by optimizing weights utilized by machine-learning algorithms. Loss function analysis may examine the cost of the difference between estimated values, to calculate the difference between hypothetical and real values. Computing device 104 may utilize factors to model relationships between past interactions between a user and system 100 and alimentary instruction sets. In an embodiment loss function analysis may utilize any factors contained within factor database 172. Loss function analysis may be user specific so as to create algorithms and outputs that are customize to factors for an individual user. Factors may include any of the factors as described herein. User behaviors and user past responses may be utilized as training data to generate outputs. Factors contained within loss function analysis may be weighted and given different numerical scores. Factors may be stored and utilized to predict subsequent outputs.

Figure 2:
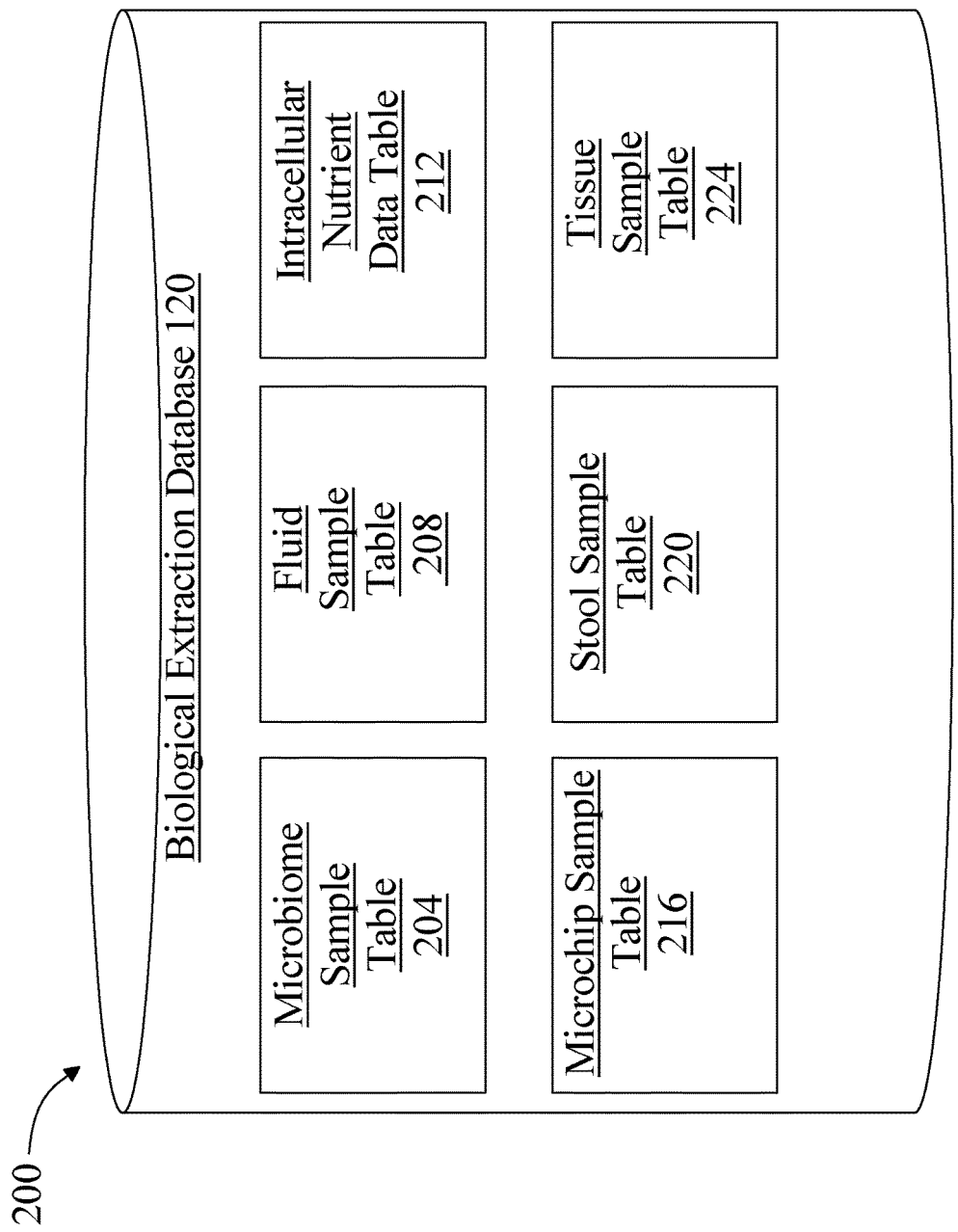
FIG. 2 is a block diagram illustrating an exemplary embodiment of a biological extraction database.

Referring now to FIG. 2, an exemplary embodiment 200 of biological extraction database 120 is illustrated. Biological extraction database 120 may be implemented as a data structure as described above in reference to FIG. 1. Biological extraction database 120 may include one or more elements of physiological data pertaining to a particular user. Physiological data contained within biological extraction database 120 may be organized according to type of biological extraction 116 utilized to analyze a particular element of physiological data, body system or body dimension that a particular element of physiological data pertains to, sample type, category of physiological data and the like. One or more tables contained within biological extraction database 120 may include microbiome sample table 204; microbiome sample table 204 may contain one or more elements of physiological data containing a microbiome sample. For instance and without limitation, microbiome sample table 204 may contain an element of physiological data such as a stool sample analyzed for levels of pathogenic bacteria. One or more tables contained within biological extraction database 120 may include fluid sample table 208; fluid sample table 208 may contain one or more elements of physiological data containing a fluid sample. For instance and without limitation, fluid sample table 208 may include a saliva sample analyzed for one or more hormone levels. One or more tables contained within biological extraction database 120 may include intracellular nutrient data table 212; intracellular nutrient data table 212 may include one or more elements of physiological data containing an intracellular nutrient level. For instance and without limitation, intracellular nutrient data table 212 may include an intracellular level of Vitamin C. One or more tables contained within biological extraction database 120 may include microchip sample table 216; microchip sample table 216 may include one or more elements of physiological data obtained from a microchip. For instance and without limitation, microchip sample table 216 may include one or more extracellular nutrient levels of coenzyme Q 10 obtained from a microchip embedded under the skin. One or more tables contained within biological extraction database 120 may include stool sample table 220; stool sample table 220 may include one or more elements of physiological data obtained from a stool sample. For instance and without limitation, stool sample table 220 may include a measurement of a stool pH level. One or more tables contained within biological extraction database 120 may include tissue sample table 224; tissue sample table 224 may include one or more elements of physiological data obtained from a tissue sample. For instance and without limitation, tissue sample table 224 may include an intestinal biopsy analyzed for the presence or absence of Celiac disease.

Figure 3:
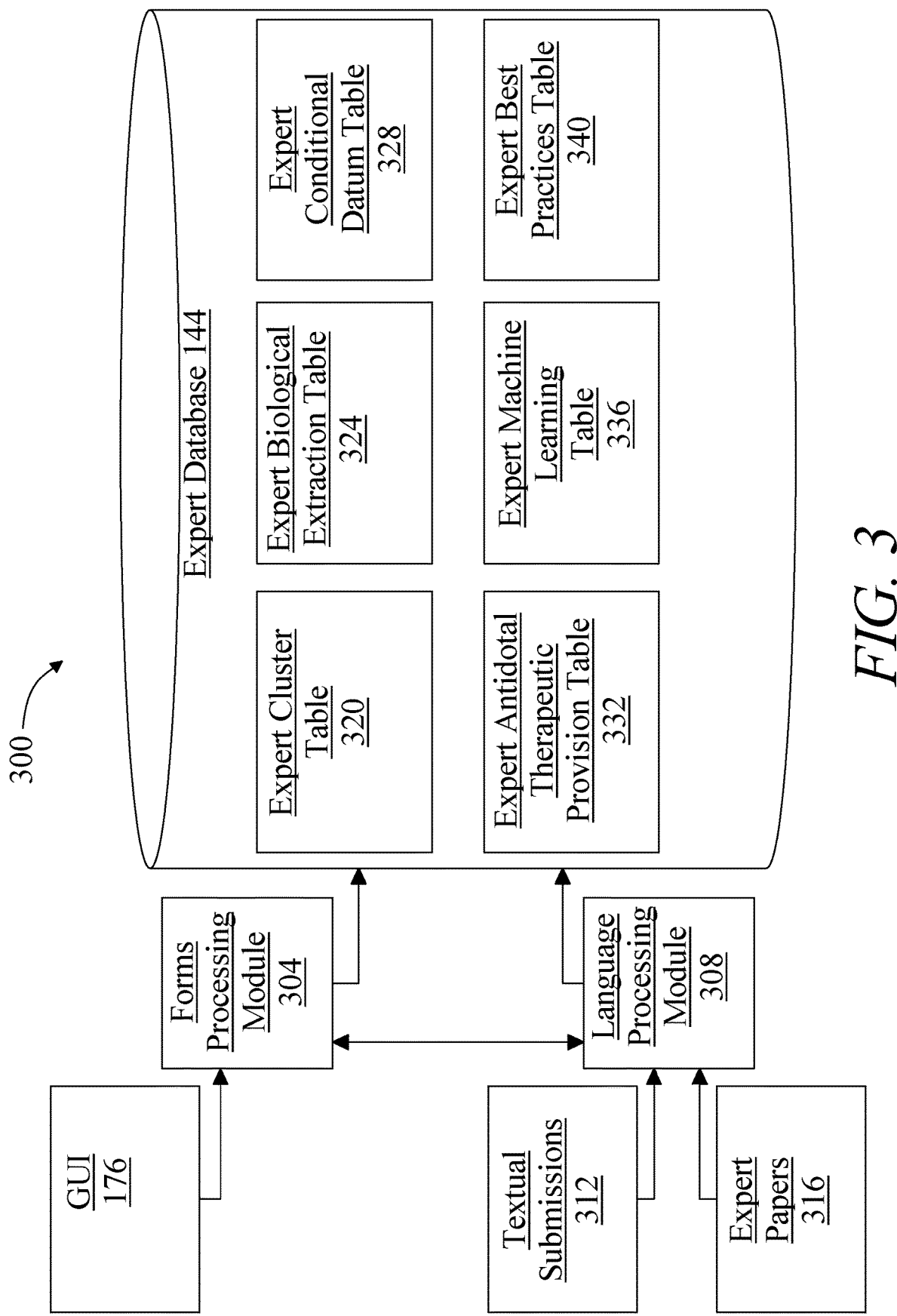
FIG. 3 is a block diagram illustrating an exemplary embodiment of an expert database.

Referring now to FIG. 3, an exemplary embodiment 300 of expert database 144 is illustrated. Expert database 144 may be implemented as any data structure suitable for use as biological extraction database 120 as described above in reference to FIG. 1. One or more database tables may be linked to one another by, for instance, common column values. For instance, a common column between two tables of expert database 144 may include an identifier of an expert submission, such as a form entry, textual submission, expert paper, or the like, for instance as defined below; as a result, a query may be able to retrieve all rows from any table pertaining to a given submission or set thereof. Other columns may include any other category usable for organization or subdivision of expert data, including types of expert data, names and/or identifiers of experts submitting the data, times of submission, or the like; persons skilled in the art, upon reviewing the entirety of this disclosure, will be aware of various ways in which expert data may be included in one or more tables.

With continued reference to FIG. 3, expert database 144 includes a forms processing module 304 that may sort data entered in a submission via graphical user interface 176 by, for instance, sorting data from entries in the graphical user interface 176 to related categories of data; for instance, data entered in an entry relating in the graphical user interface 176 to a clustering algorithm may be sorted into variables and/or data structures for storage of clustering algorithms, while data entered in an entry relating to a category of training data and/or an element thereof may be sorted into variables and/or data structures for the storage of, respectively, categories of training data. Where data is chosen by an expert from pre-selected entries such as drop-down lists, data may be stored directly; where data is entered in textual form, language processing module 308 may be used to map data to an appropriate existing label, for instance using a vector similarity test or other synonym-sensitive language processing test to map physiological data to an existing label. Alternatively or additionally, when a language processing algorithm, such as vector similarity comparison, indicates that an entry is not a synonym of an existing label, language processing module 308 may indicate that entry should be treated as relating to a new label; this may be determined by, e.g., comparison to a threshold number of cosine similarity and/or other geometric measures of vector similarity of the entered text to a nearest existent label, and determination that a degree of similarity falls below the threshold number and/or a degree of dissimilarity falls above the threshold number. Data from expert textual submissions 312, such as accomplished by filling out a paper or PDF form and/or submitting narrative information, may likewise be processed using language processing module 308. Data may be extracted from expert papers 316, which may include without limitation publications in medical and/or scientific journals, by language processing module 308 via any suitable process as described herein. Persons skilled in the art, upon reviewing the entirety of this disclosure, will be aware of various additional methods whereby novel terms may be separated from already-classified terms and/or synonyms therefore, as consistent with this disclosure.

With continued reference to FIG. 3, one or more tables contained within expert database 144 may include expert cluster table 320; expert cluster table 320 may include one or more expert inputs related to one or more clustering algorithms and/or k values. One or more tables contained within expert database 144 may include expert biological extraction table 324; expert biological extraction table 324 may include one or more expert inputs related to one or more biological extractions. One or more tables contained within expert database 144 may include expert conditional datum table 328; expert conditional datum table 328 may include one or more expert inputs related to one or more conditional datum 112. One or more tables contained within expert database 144 may include expert antidotal therapeutic provision table 332; expert antidotal therapeutic provision table 332 may include one or more expert inputs related to one or more antidotal therapeutic provision 132. One or more tables contained within expert database 144 may include expert machine-learning table 336; expert machine-learning table 336 may include one or more expert inputs related to machine-learning. One or more tables contained within expert database 144 may include expert factor table 340; expert factor table 340 may include one or more expert inputs related to one or more expert factors.

Figure 4:
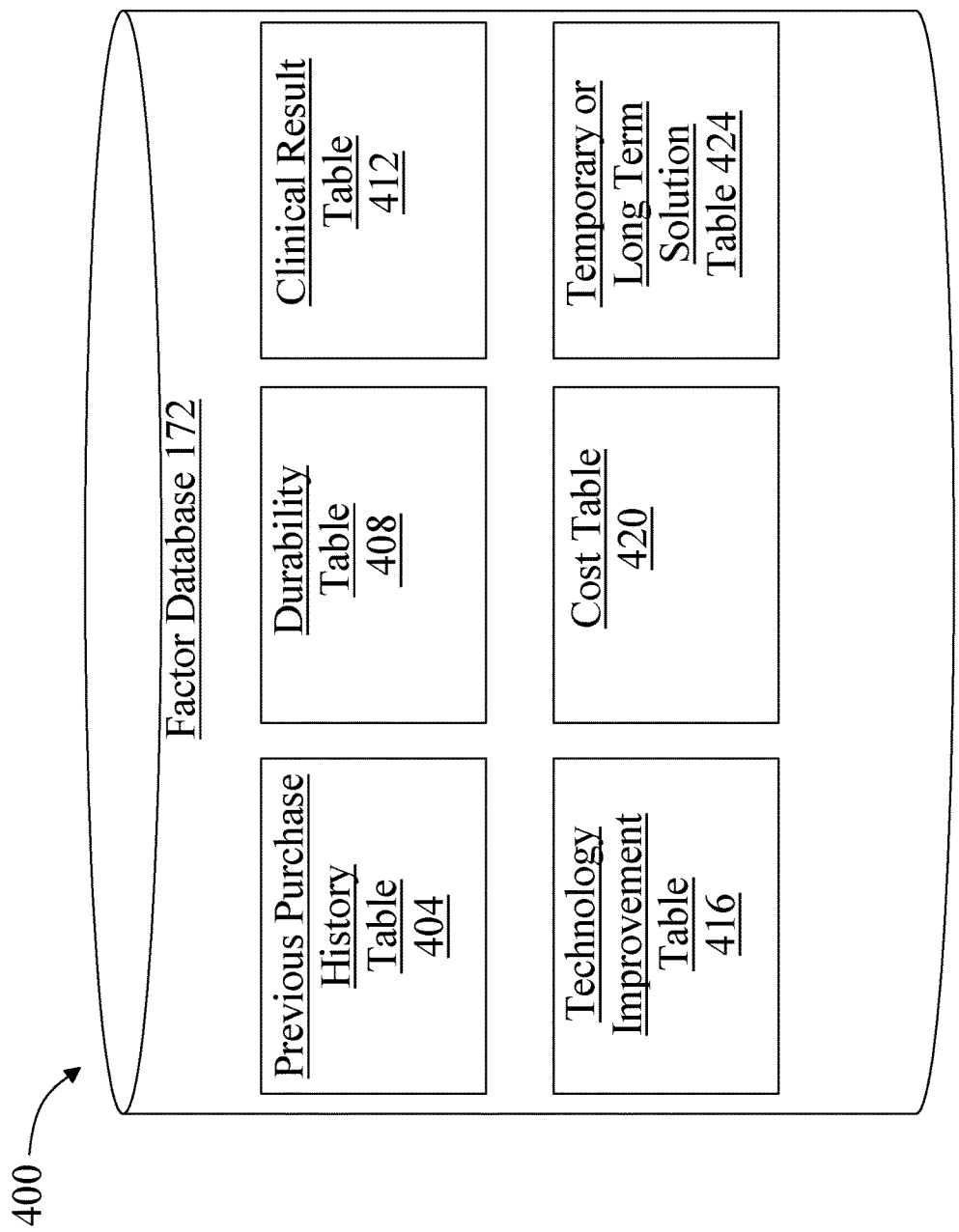
FIG. 4 is a block diagram illustrating an exemplary embodiment of a factor database.

Referring now to FIG. 4, an exemplary embodiment 400 of factor database 172 is illustrated. Factor database 172 may be implemented as any data structure suitable for use as biological extraction database 120 as described above in more details in reference to FIG. 1. One or more tables contained within factor database 172 may include previous purchase history table 404; previous purchase history table 404 may include one or more factors related to previous antidotal therapeutic provision purchases. For instance and without limitation, previous purchase history table 404 may include an entry that describes a particular brand of gauze that a user has bought on three separate occasions. One or more tables contained within factor database 172 may include durability table 408; durability table 408 may include one or more factors related to antidotal therapeutic provision durability. For instance and without limitation, durability table 408 may include an entry that describes the durability of a particular brand pacemaker as lasting no more than ten years. One or more tables contained within factor database 172 may include clinical results table 412; clinical results table 412 may include one or more factors related to clinical results of one or more antidotal therapeutic provision 132. For instance and without limitation, clinical results table 412 may describe the recent clinical results of an insulin pump. One or more tables contained within factor database 172 may include technology improvement table 416; technology improvement table 416 may describe any technological improvement of any antidotal therapeutic provision 132. For instance and without limitation, technology improvement table 416 may describe a technological improvement of a glucometer that uses microneedles to take less blood while testing a user's blood glucose levels. One or more tables contained within factor database 172 may include clinical results table 416; clinical results table 416 may include a description of one or more clinical results that one or more antidotal therapeutic provision 132 can achieve. For instance and without limitation, clinical results table 416 may describe a walker that achieves a clinical result to improve one's posture and reduce the risk of falls. One or more tables contained within factor database 172 may include cost table 420; cost table 420 may include one or more factors related to cost. For instance and without limitation, cost table 420 may describe a cost of an antidotal therapeutic provision 132 or how much money a user is willing to spend on an antidotal therapeutic provision 132. One or more tables contained within factor database 172 may include temporary or long term solution table 424; temporary or long term solution table 424 may describe if a particular antidotal therapeutic provision 132 is a temporary solution or if a particular antidotal therapeutic provision 132 is a long term solution. For instance and without limitation, temporary or long term solution table 424 may describe a stent intended to be implanted in one's artery as being a long term solution to coronary artery disease.

Figure 5:
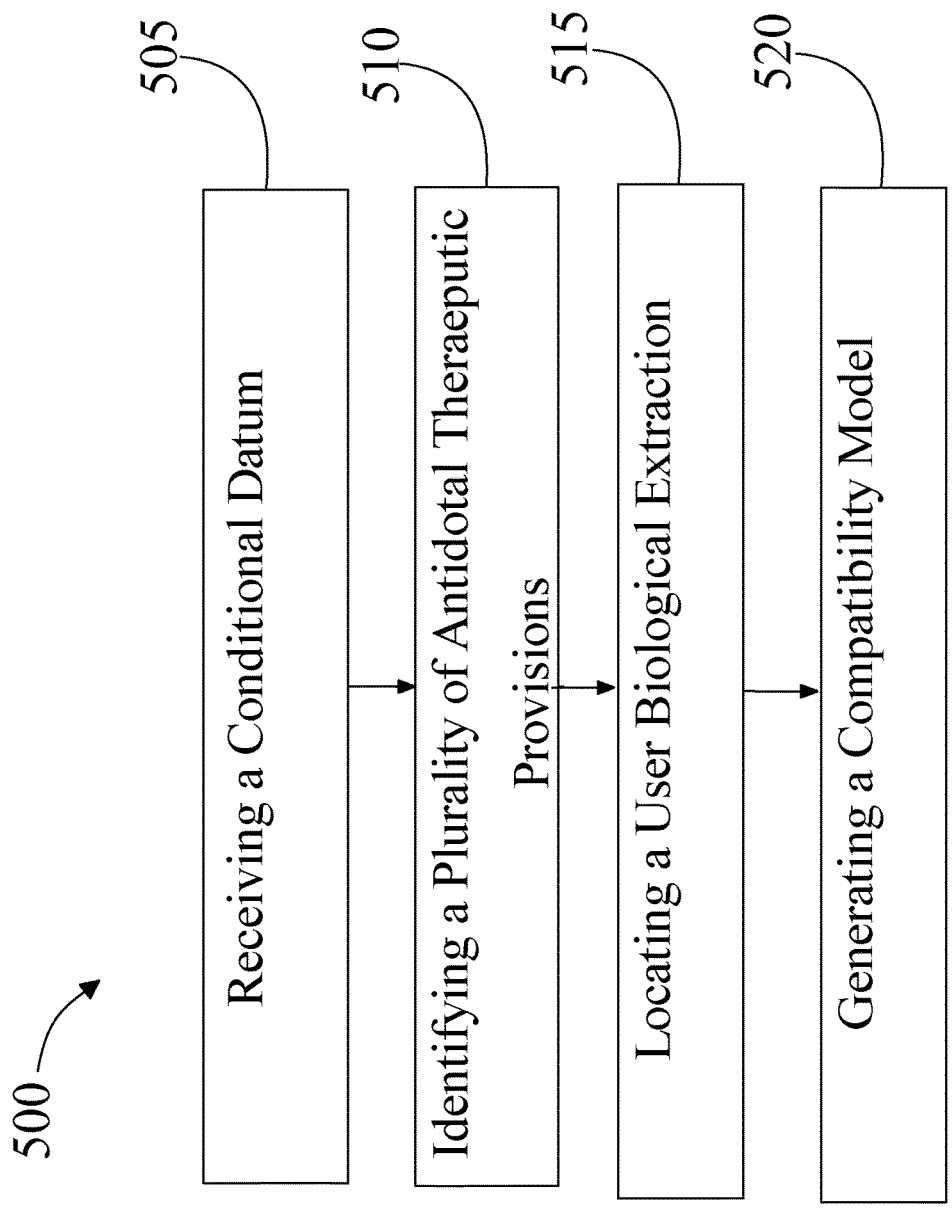
FIG. 5 is a process flow diagram illustrating an exemplary embodiment of a method of physiologically informed therapeutic provisions.

Referring now to FIG. 5, an exemplary embodiment of a method 500 of physiologically informed therapeutic provisions is illustrated. At step 505 computing device 104 receives from a remote device 108 operated by a user, a conditional datum 112 wherein the conditional datum 112 contains a description of a current bodily complaint. Computing device 104 receives a conditional datum 112 utilizing any network methodology as described herein. A conditional datum 112 contains data describing a current bodily complaint as described above in more detail in reference to FIG. 1. For example, a conditional datum 112 may describe a user's dull and aching left hip pain that occurs with movement. In yet another non-limiting example, a conditional datum 112 may describe hypoglycemia episode a user experiences three mornings each week upon waking. In yet another non-limiting example, a conditional datum 112 may describe a diagnosis of an acute medical condition such as acute kidney failure. In yet another non-limiting example, a conditional datum 112 may describe a diagnosis of a chronic medical condition such as rheumatoid arthritis or asthma. In yet another non-limiting example, a conditional datum 112 may describe a medical condition that is in remission, such as Chron's disease that has stabilized and not caused any flare ups. Computing device 104 may receive a conditional datum 112 from a remote device 108 operated by an informed advisor. For instance and without limitation, computing device 104 may receive a conditional datum 112 containing a current bodily diagnosis such as hashimoto's thyroiditis from a user's endocrinologist. In yet another non-limiting example, computing device 104 may receive a conditional datum 112 containing a diagnosis of generalized anxiety disorder from a remote device 108 operated by a user's functional medicine practitioner. In yet another non-limiting example, computing device 104 may receive a conditional datum 112 containing a diagnosis of a frozen shoulder from a remote device 108 operated by a user's massage therapist.

With continued reference to FIG. 5, computing device 104 may identify a conditional datum 112 utilizing one or more machine-learning processes and/or algorithms. This may occur for example, when a user is not aware of any conditions they may be currently suffering from, or when a user's informed advisor has not diagnosed the user with any medical conditions and/or diagnoses. In yet another non-limiting example, computing device 104 may utilize one or more machine-learning processes and/or algorithms to aid an informed advisor surrounding a diagnosis and/or to confirm the findings of an informed advisor and provide a second opinion. Computing device 104 may generate a conditional datum 112 utilizing one or more machine-learning algorithms and/or processes by first retrieving a biological extraction 116 pertaining to a user. One or more user biological extraction 116 may be stored within biological extraction database 120 as described above in more detail in reference to FIGS. 1-4. For instance and without limitation, computing device 104 may retrieve a biological extraction 116 pertaining to a user that contains a stool sample analyzed for one or more strains of pathogenic bacteria such as *Clostridium difficile* and Campylobacteria. In yet another non-limiting example, computing device 104 may retrieve a biological extraction 116 pertaining to a user that contains results from a saliva sample analyzed for different hormone levels including estrone, estradiol, estriol, progesterone, testosterone, cortisol, and melatonin. Computing device 104 may retrieve one or more biological extraction 116 pertaining to a user based on one or more expert inputs stored within expert database 144. Computing device 104 receives conditional training data 124. Conditional training data 124 includes any of the conditional training data 124 as described above in reference to FIGS. 1-4. Conditional training data 124 includes a plurality of biological extraction 116 and a plurality of correlated conditions. Computing device 104 generates a conditional model 128 utilizing the user biological extraction 116 and the conditional training data 124. Conditional model 128 includes any of the conditional model 128 as described above in reference to FIGS. 1-4. Conditional model 128 includes a biological extraction 116 as an input and outputs a conditional datum 112 containing a suspected condition. A suspected condition includes any of the suspected conditions as described above in reference to FIGS. 1-4. For instance and without limitation, computing device 104 may utilize a user's biological extraction 116 that contains a fasting blood glucose of 135 milligrams per deciliter and a microbiome sample that contains a disruption of the gut flora to contain an overgrowth of pathogenic bacteria that carry lipopolysaccharide (LPS), as an input to conditional model 128, and utilize conditional training data 124 to generate an output that contains a conditional datum 112 containing Type 2 Diabetes Mellites.

With continued reference to FIG. 5, at step 510 computing device 104 identifies a plurality of antidotal therapeutic provision 132. Antidotal therapeutic provision 132 includes any health care material, product, and/or device prescribed and/or recommended by an informed advisor, used to serve a medical purpose as described above in more detail in reference to FIG. 1. For example, an antidotal therapeutic provision 132 may include a medical device such as a hip implant, an interocular lens, an implantable insulin pump, a cardiac pacemaker, an implantable cardiac defibrillator and the like. An antidotal therapeutic provision may include one or more medical supplies such as a syringe, a dressing, gauze, a catheter, a thermometer, a cotton swab, a nebulizer, a glucose meter, a humidifier, an infusion pump, a feeding tube, and the like. Computing device 104 identifies a plurality of antidotal therapeutic provision 132 using a therapeutic clustering model 136. Therapeutic clustering model 136 includes any of the therapeutic clustering model 136 as described above in reference to FIGS. 1-4. Therapeutic clustering model 136 utilizes a conditional datum 112 as an input and outputs antidotal therapeutic provision 132. Computing device 104 generates therapeutic clustering model 136 by receiving a clustering dataset 140. Clustering dataset 140 includes any of the clustering dataset 140 as described above in reference to FIG. 1. Clustering dataset 140 contains a plurality of unclassified cluster data entries. Computing device 104 calculates a first clustering algorithm. A first clustering algorithm includes any of the clustering algorithms as described above in reference to FIGS. 1-4. In an embodiment, first clustering algorithm may include generating a k-means clustering algorithm. K-means clustering algorithm includes any of the k-means clustering algorithms as described above in reference to FIGS. 1-4. In an embodiment, k value utilized in a k-means clustering algorithm based on one or more expert inputs contained within expert database 144. In an embodiment, first clustering algorithm may include generating a hierarchical clustering algorithm. Hierarchical clustering algorithm includes any of the hierarchical clustering algorithms as described above in reference to FIGS. 1-4. Computing device 104 may select a first clustering algorithm based on one or more inputs contained within expert database 144. For example, an expert input may specify that a conditional datum 112 that contains a condition such as coronary artery disease may be best suited for a first clustering algorithm such as a density based clustering algorithm, while a conditional datum 112 that contains a condition such as acne vulgaris may be best suited for a first clustering algorithm such as an agglomerative hierarchical clustering algorithm.

With continued reference to FIG. 5, computing device 104 may analyze one or more of the plurality of output antidotal therapeutic provisions generated by therapeutic clustering model 136. Computing device 104 may analyze the plurality of output antidotal therapeutic provision 132 by calculating a user effective age 148. A user effective age 148 is an age of a user as adjusted to reflect a life expectancy that differs from an actuarially projected life expectancy, as described above in more detail in reference to FIG. 1. A user effective age 148 may be calculated using a user chronological age and a user biological extraction 116. Computing device 104 analyzes output antidotal therapeutic provision 132 utilizing a user effective age 148. For example, an output antidotal therapeutic provision 132 for a pacemaker that needs to be replaced after a maximum of 5 years may not be suitable for a user who has an effective age of 88 years old. In yet another non-limiting example, an output antidotal therapeutic provision 132 for an insulin pump that may last for up to ten years may be suitable for a user who has an effective age of fifteen years old. Computing device 104 may analyze any of the plurality of output antidotal therapeutic provisions by consulting factor database 172. For example, computing device 104 may retrieve a factor pertaining to cost and compare the cost of two different antidotal therapeutic provisions based on how much money a user is willing to spend on an antidotal therapeutic provision 132. For example, a factor stored within factor database 172 may indicate that a user is willing to spend up to $500 on any given antidotal therapeutic provision 132. In such an instance, computing device 104 may utilize a cost benefit analysis based on a user's effective age to select a particular antidotal therapeutic provision 132. For example, computing device 104 may compare a one-time cardiac ablation treatment that will cost the user $1000 and solve the problem, versus a pacemaker that will cost $500 and need to be replaced in six to eight years' time, for a user who has an effective age of thirty six. In yet another non-limiting example, computing device 104 may compare a syringe that costs $1 per day to accurately measure a dose of insulin versus an insulin pump that costs $250 and will last up to ten years for a user who has an effective age of twelve.

With continued reference to FIG. 5, at step 515, computing device 104 is configured to locate a user biological extraction 116 wherein the user biological extraction 116 contains at least an element of user physiological data. Computing device 104 may store one or more user biological extraction 116 pertaining to a user within biological extraction database 120. Computing device 104 may locate a user biological extraction 116 by inputting a conditional datum to a biological classifier 152. Biological classifier 152 may be generated utilizing a classification algorithm. Classification algorithm includes any of the classification algorithms as described above in reference to FIGS. 1-4. Computing device 104 may input a conditional datum to biological classifier 152 and output related biological extraction 116. Biological extraction 116 may be related to a conditional datum 112 when they may be used to treat, manage, track, mitigate, diagnose, and/or monitor a conditional datum 112 as described above in more detail in reference to FIG. 1. For instance and without limitation, computing device 104 may input a conditional datum 112 such as hypothyroidism to biological classifier 152 and output related biological extraction 116 that include a blood sample containing a thyroid stimulating hormone, total thyroxine (T4), triiodothyronine (T3) uptake, total T3, Free T4, Free T3, Reverse T3, and thyroid antibodies. In yet another nonlimiting example, computing device 104 may input a conditional datum 112 such as small intestinal bacterial overgrowth (SIBO) to biological classifier 152 and output related biological extraction 116 that include a lactulose breath test, endoscopy with cultures of small intestine bacteria, and/or a glucose breath test. Computing device 104 locates one or more of output biological extraction 116 related to a conditional datum 112 and generates compatibility model 156 utilizing the biological extraction 116 related to the conditional datum 112. Computing device 104 may located a biological extraction 116 related to a conditional datum 112 within biological extraction database 120.

With continued reference to FIG. 5, at step 520 computing device 104 generates a compatibility model 156. Compatibility model 156 includes any of the compatibility model 156 as described above in reference to FIG. 1. Compatibility model 156 incudes any machine-learning model as described above in reference to FIGS. 1-4. For example, compatibility model 156 may include a supervised machine-learning algorithm, an unsupervised machine-learning algorithm, and/or a lazy learning model. Computing device 104 may generate compatibility model 156 as a particular machine-learning algorithm based on one or more expert inputs stored within expert database 144. Compatibility model 156 utilizes antidotal therapeutic provision 132 and a user biological extraction 116 as an input and outputs compatible antidotal therapeutic provision 160. Compatible antidotal therapeutic provision 160 include any antidotal therapeutic provision 132 that is proper to be used based on both a user's biological extraction 116 and a user's conditional datum 112. For instance and without limitation, computing device 104 may determine that an antidotal therapeutic provision such as a particular brand gauze is not proper for a user based on a user's biological extraction 116 because even though the gauze would be appropriate for the user's flesh wound, it contains an ingredient that may cause further toxicity within the user's body because the user's biological extraction 116 indicates that the user has impaired metabolism of xenoestrogens due to a mutation in a gene controlling methylation pathways in the body. In yet another non-limiting example, computing device 104 may determine that an antidotal therapeutic provision 132 such as a particular glucometer is proper for a user based on a user's biological extraction 116 because the glucometer is compatible based on the user's biological extraction 116 and the user's previous diagnosis of insulin resistance.

With continued reference to FIG. 5, computing device 104 may generate compatibility model 156 utilizing compatibility training data 164. Compatibility training data 164 includes any of the training data as described above in reference to FIGS. 1-4. Compatibility training data 164 includes a plurality of therapeutic provisions and biological extraction 116 as inputs and outputs compatible antidotal therapeutic provision 160. Compatibility training data may be generated based on one or more expert inputs contained within expert database 144. Computing device 104 calculates a compatibility model 156 utilizing compatibility training data 164 and using a first machine-learning algorithm. First machine-learning algorithm includes any of the machine-learning algorithms as described above in reference to FIGS. 1-4. For instance and without limitation, first machine-learning algorithm may include a supervised machine-learning algorithm. In yet another non-limiting example, first machine-learning algorithm may include an unsupervised machine-learning algorithm. Computing device 104 may select a first machine-learning algorithm based on one or more expert inputs contained within expert database 144. Computing device 104 may output compatible antidotal therapeutic provisions utilizing one or more factor 168. A factor 168 includes any variable that may be utilized to generate compatibility model 156 and output compatible antidotal therapeutic provision 160. Factor 168 may be stored within factor database 172 as described above in more detail in reference to FIGS. 1-4. A factor 168 may be generated by a user, an informed advisor, and/or an expert input. A factor 168 may indicate the previous user purchase history of one or more compatible antidotal therapeutic provisions. For example, a factor 168 may indicate a particular brand pacemaker that a user had surgically implanted into an artery five years prior. In yet another non-limiting example, a factor 168 may indicate a particular brand left shoulder replacement that a user had implanted three months prior. A factor 168 may indicate the durability of any antidotal therapeutic provision 132, such as how long it is intended to last and how frequently it may need to be replaced. A factor 168 may indicate the cost of any antidotal therapeutic provision 132, including how much money a user may have to pay out of pocket and how much an insurance company may cover for an antidotal therapeutic provision 132. A factor 168 may indicate clinical results achieved by any antidotal therapeutic provision 132 in any recent research and clinical work. A factor 168 may indicate any technological improvement that an antidotal therapeutic provision 132 may obtain or achieve as compared to previous generation or older model antidotal therapeutic provisions. A factor 168 may indicate the ease of use of an antidotal therapeutic provision 132. A factor 168 may indicate if an antidotal therapeutic provision 132 solves a problem and is a permanent fix for a conditional datum 112 or if an antidotal therapeutic provision 132 is only a temporary solution and will need to be replaced in any upcoming years. Computing device 104 retrieves a factor 168 related to an antidotal therapeutic provision 132 from factor database 172. Computing device 104 generates a compatibility model 156 utilizing a factor 168. In an embedment, a factor 168 may be utilized as an input to compatibility model 156. Computing device 104 outputs compatible antidotal therapeutic provision 160 utilizing a factor 168. In an embodiment, computing device 104 may utilize one or more factor 168 to generate additional machine-learning algorithms. Computing device 104 may utilize one or more factor 168 to generate a loss function as described above in reference to FIG. 1.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 6:
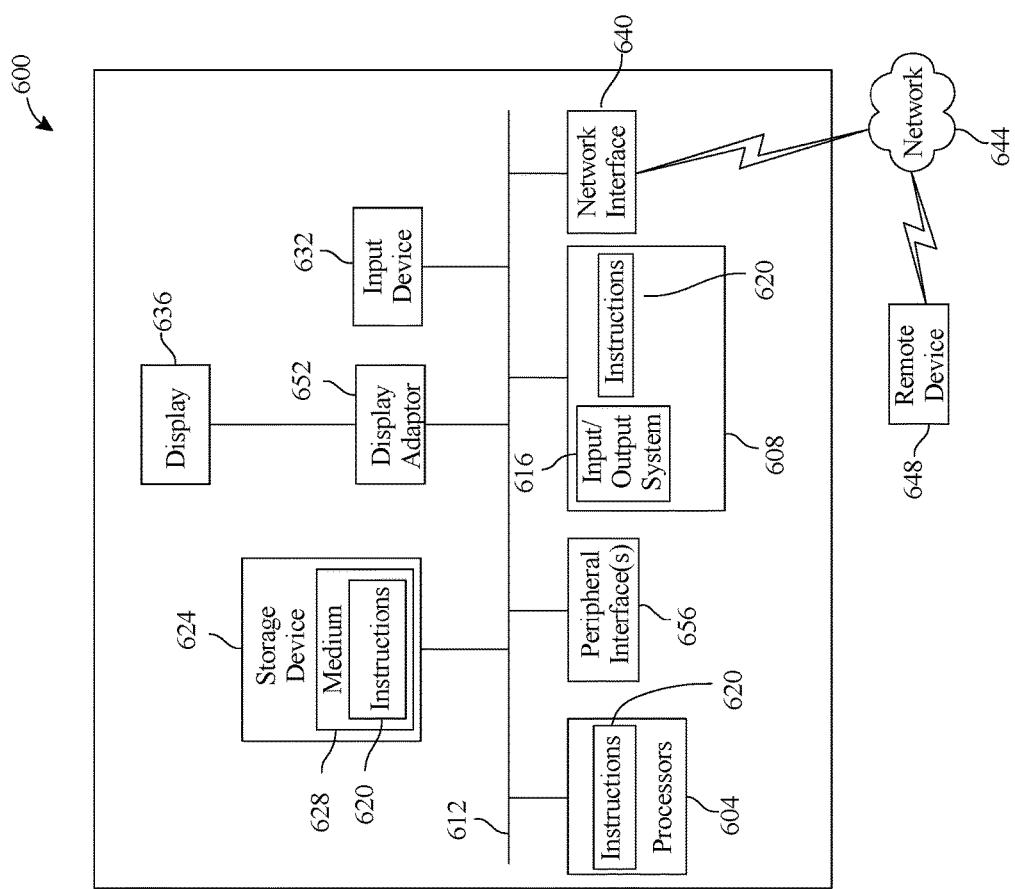
FIG. 6 is a block diagram of a computing system that can be used to implement any one or more of the methodologies disclosed herein and any one or more portions thereof.

FIG. 6 shows a diagrammatic representation of one embodiment of a computing device in the exemplary form of a computer system 600 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 600 includes a processor 604 and a memory 608 that communicate with each other, and with other components, via a bus 612. Bus 612 may include any of several types of bus structures including, but not limited to, a memory bus, a memory controller, a peripheral bus, a local bus, and any combinations thereof, using any of a variety of bus architectures.

Memory 608 may include various components (e.g., machine-readable media) including, but not limited to, a random access memory component, a read only component, and any combinations thereof. In one example, a basic input/output system 616 (BIOS), including basic routines that help to transfer information between elements within computer system 600, such as during start-up, may be stored in memory 608. Memory 608 may also include (e.g., stored on one or more machine-readable media) instructions (e.g., software) 620 embodying any one or more of the aspects and/or methodologies of the present disclosure. In another example, memory 608 may further include any number of program modules including, but not limited to, an operating system, one or more application programs, other program modules, program data, and any combinations thereof.

Computer system 600 may also include a storage device 624. Examples of a storage device (e.g., storage device 624)

include, but are not limited to, a hard disk drive, a magnetic disk drive, an optical disc drive in combination with an optical medium, a solid-state memory device, and any combinations thereof. Storage device 624 may be connected to bus 612 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 624 (or one or more components thereof) may be removably interfaced with computer system 600 (e.g., via an external port connector (not shown)). Particularly, storage device 624 and an associated machine-readable medium 628 may provide nonvolatile and/or volatile storage of machine-readable instructions, data structures, program modules, and/or other data for computer system 600. In one example, software 620 may reside, completely or partially, within machine-readable medium 628. In another example, software 620 may reside, completely or partially, within processor 604.

Computer system 600 may also include an input device 632. In one example, a user of computer system 600 may enter commands and/or other information into computer system 600 via input device 632. Examples of an input device 632 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 632 may be interfaced to bus 612 via any of a variety of interfaces (not shown) including, but not limited to, a serial interface, a parallel interface, a game port, a USB interface, a FIREWIRE interface, a direct interface to bus 612, and any combinations thereof. Input device 632 may include a touch screen interface that may be a part of or separate from display 636, discussed further below. Input device 632 may be utilized as a user selection device for selecting one or more graphical representations in a graphical interface as described above.

A user may also input commands and/or other information to computer system 600 via storage device 624 (e.g., a removable disk drive, a flash drive, etc.) and/or network interface device 640. A network interface device, such as network interface device 640, may be utilized for connecting computer system 600 to one or more of a variety of networks, such as network 644, and one or more remote devices 648 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 644, may employ a wired and/or a wireless mode of communication. In general, any network topology may be used. Information (e.g., data, software 620, etc.) may be communicated to and/or from computer system 600 via network interface device 640.

Computer system 600 may further include a video display adapter 652 for communicating a displayable image to a display device, such as display device 636. Examples of a display device include, but are not limited to, a liquid crystal display (LCD), a cathode ray tube (CRT), a plasma display, a light emitting diode (LED) display, and any combinations thereof. Display adapter 652 and display device 636 may be utilized in combination with processor 604 to provide graphical representations of aspects of the present disclosure. In addition to a display device, computer system 600 may include one or more other peripheral output devices including, but not limited to, an audio speaker, a printer, and any combinations thereof. Such peripheral output devices may be connected to bus 612 via a peripheral interface 656. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for physiologically informed therapeutic provisions, the system comprising a computing device, the computing device designed and configured to:
   receive, from a remote device operated by a user:
      a conditional datum, wherein the conditional datum contains a description of a current bodily complaint; and
      a factor, wherein the factor describes at least a budgetary constraint of the user for a particular antidotal therapeutic provision;
   identify a plurality of antidotal therapeutic provisions, using a therapeutic clustering model, wherein the therapeutic clustering model utilizes the conditional datum as an input and outputs the plurality of antidotal therapeutic provisions;
   locate a first user biological extraction, wherein the first user biological extraction contains at least an element of user physiological data;
   train, using compatibility training data and a machine-learning algorithm, a compatibility machine-learning model, wherein the compatibility training data comprises antidotal therapeutic data and biological extraction data correlated with compatible antidotal therapeutic data; and
   generate, using the trained compatibility machine-learning model, at least a compatible antidotal therapeutic provision, wherein the plurality of antidotal therapeutic provisions, the factor and the first user biological extraction are provided to the trained compatibility machine-learning model as inputs to output the at least a compatible antidotal therapeutic provision.

2. The system of claim 1, wherein the computing device is further configured to:
   retrieve a second user biological extraction;
   receive conditional training data, wherein the conditional training data contains a plurality of biological extractions and a plurality of correlated conditions; and
   generate a conditional model, wherein the conditional model utilizes the second user biological extraction as an input and outputs the conditional datum containing a suspected condition.

3. The system of claim 1, wherein the computing device is further configured to receive from the remote device, operated by an informed advisor, the conditional datum containing a current bodily diagnosis.

4. The system of claim 1, wherein the computing device is further configured to identify the plurality of antidotal therapeutic provisions using the therapeutic clustering model by:
   receiving a clustering dataset, wherein the clustering dataset further comprises a plurality of unclassified cluster data entries; and
   calculating a first clustering algorithm.

5. The system of claim 4, wherein the first clustering algorithm further comprises a k-means clustering algorithm.

6. The system of claim 4, wherein the first clustering algorithm further comprises a hierarchical clustering algorithm.

7. The system of claim 1, wherein the computing device is further configured to:
   calculate a user effective age utilizing a user chronological age and a third user biological extraction; and
   analyze output antidotal therapeutic provisions as a function of the user effective age.

8. The system of claim 1, wherein the computing device is further configured to:
   input the conditional datum to a biological classifier, the biological classifier configured to input conditional datums and output related biological extractions by executing a classification algorithm;
   locate a fourth user biological extraction related to the conditional datum; and
   generate the compatibility model utilizing the fourth user biological extraction related to the conditional datum.

9. The system of claim 1, wherein the system further comprises a sensor configured to detect the at least an element of user physiological data.

10. A method of physiologically informed therapeutic provisions, the method comprising:
    receiving, by a computing device, from a remote device operated by a user:
      a conditional datum, wherein the conditional datum contains a description of a current bodily complaint; and
      a factor, wherein the factor describes at least a budgetary constraint of the user for a particular antidotal therapeutic provision;
    identifying, by the computing device, a plurality of antidotal therapeutic provisions, using a therapeutic clustering model, wherein the therapeutic clustering model utilizes the conditional datum as an input and outputs the plurality of antidotal therapeutic provisions
    locating, by the computing device, a first user biological extraction, wherein the first user biological extraction contains at least an element of user physiological data;
    training, by the computing device, using compatibility training data and a machine-learning algorithm, a compatibility machine-learning model, wherein the compatibility training data comprises antidotal therapeutic data and biological extraction data correlated with compatible antidotal therapeutic data; and
    generating, by the computing device, using the trained compatibility machine-learning model, at least a compatible antidotal therapeutic provision, wherein the plurality of antidotal therapeutic provisions, the factor and the first user biological extraction are provided to the trained compatibility machine-learning model as inputs to output the at least a compatible antidotal therapeutic provision.

11. The method of claim 10, wherein receiving the conditional datum further comprises:
    retrieving a second user biological extraction;
    receiving, conditional training data, wherein the conditional training data contains a plurality of biological extractions and a plurality of correlated conditions; and
    generating a conditional model, wherein the conditional model utilizes the second user biological extraction as an input and outputs the conditional datum containing a suspected condition.

12. The method of claim 10, wherein receiving the conditional datum further comprises receiving from the remote device, operated by an informed advisor, the conditional datum containing a current bodily diagnosis.

13. The method of claim 10, wherein identifying the plurality of antidotal therapeutic provisions further comprises:
    receiving a clustering dataset, wherein the clustering dataset further comprises a plurality of unclassified cluster data entries; and
    calculating a first clustering algorithm.

14. The method of claim 13, wherein calculating the first clustering algorithm further comprises calculating a k-means clustering algorithm.

15. The method of claim 13, wherein calculating the first clustering algorithm further comprises calculating a hierarchical clustering algorithm.

16. The method of claim 10, wherein identifying the plurality of antidotal therapeutic provisions further comprises:
    calculating a user effective age utilizing a user chronological age and a third user biological extraction; and
    analyzing output antidotal therapeutic provisions as a function of the user effective age.

17. The method of claim 10, wherein locating the biological extraction further comprises:
    inputting the conditional datum to a biological classifier, the biological classifier configured to input conditional datums and output related biological extractions by executing a classification algorithm;
    locating a fourth user biological extraction related to the conditional datum; and
    generating the compatibility model utilizing the fourth user biological extraction related to the conditional datum.

18. The method of claim 10, wherein the method further comprises detecting, by a sensor, the at least an element of user physiological data.

* * * * *